United States Patent
Hashizume

(10) Patent No.: US 11,796,497 B2
(45) Date of Patent: Oct. 24, 2023

(54) ODOR SENSOR AND ODOR MEASUREMENT SYSTEM

(71) Applicant: AROMA BIT, INC., Tokyo (JP)

(72) Inventor: Kenichi Hashizume, Tokyo (JP)

(73) Assignee: AROMA BIT, INC.

(*) Notice: Subject to any disclaimer, the term of this patent is extended or adjusted under 35 U.S.C. 154(b) by 112 days.

(21) Appl. No.: 17/343,861

(22) Filed: Jun. 10, 2021

(65) Prior Publication Data
US 2021/0302347 A1    Sep. 30, 2021

Related U.S. Application Data

(63) Continuation of application No. 15/982,699, filed on May 17, 2018, now Pat. No. 11,073,491, which is a
(Continued)

(30) Foreign Application Priority Data

Nov. 17, 2015    (WO) .................. PCT/JP2015/082326

(51) Int. Cl.
*G01N 27/00*    (2006.01)
*G01N 27/12*    (2006.01)
(Continued)

(52) U.S. Cl.
CPC .............. *G01N 27/126* (2013.01); *G01N 5/02* (2013.01); *G01N 27/227* (2013.01);
(Continued)

(58) Field of Classification Search
CPC ...... G01N 27/126; G01N 5/02; G01N 27/227; G01N 27/4141; G01N 33/0031;
(Continued)

(56) References Cited

U.S. PATENT DOCUMENTS 5,571,401 A    11/1996    Lewis et al.
6,631,333 B1    10/2003    Lewis et al.
(Continued)

FOREIGN PATENT DOCUMENTS

CA    2808849 A1    2/2012
EP    0821228 A1    1/1998
(Continued)

OTHER PUBLICATIONS

CN201680059047.A First Office Action dated Mar. 25, 2020, 17 pgs.
(Continued)

*Primary Examiner* — Herbert K Roberts
*Assistant Examiner* — Anthony W Megna Fuentes
(74) *Attorney, Agent, or Firm* — Bracewell LLP; Brad Y. Chin

(57) ABSTRACT

According to various embodiments, there is provided an odor sensor including at least two sensor elements each having a substance adsorbing membrane for adsorbing one or more odor substances included in air; and an electrical signal conversion unit for measuring the electrical characteristics of the substance adsorbing membrane after adsorption of the substance, in which the substance adsorbing membrane has a main skeleton containing an electroconductive polymer and contains a dopant for modifying the main skeleton of the electroconductive polymer, and the at least two sensor elements are respectively provided with substance adsorbing membranes having different proportions of the main skeleton and the dopant. Also provided is an odor measurement system using the sensor.

18 Claims, 18 Drawing Sheets

Related U.S. Application Data continuation of application No. PCT/JP2016/055082, filed on Feb. 22, 2016.

(51) Int. Cl.

| | | |
|---|---|---|
| *G01N 5/02* | (2006.01) | |
| *G01N 27/22* | (2006.01) | |
| *G01N 27/414* | (2006.01) | |
| *G01N 33/00* | (2006.01) | |
| G01N 29/02 | (2006.01) | |
| G01N 29/036 | (2006.01) | |

(52) U.S. Cl.
CPC ..... *G01N 27/4141* (2013.01); *G01N 33/0031* (2013.01); *G01N 2027/222* (2013.01)

(58) Field of Classification Search
CPC ........... G01N 2027/222; G01N 29/022; G01N 29/036; G01N 2291/0255; G01N 2291/0256; G01N 27/00
See application file for complete search history.

(56) References Cited

U.S. PATENT DOCUMENTS

| 8,394,330 | B1 | 3/2013 | Lewis et al. |
|---|---|---|---|
| 2003/0136960 | A1 | 7/2003 | Goodman et al. |
| 2004/0040841 | A1 | 3/2004 | Gonzalez-Martin et al. |
| 2008/0262743 | A1 | 10/2008 | Lewis et al. |
| 2009/0152503 | A1 | 6/2009 | Kitamura |
| 2009/0293590 | A1 | 12/2009 | Zeng et al. |
| 2012/0052395 | A1 | 3/2012 | Badre et al. |

FOREIGN PATENT DOCUMENTS

| EP | 0950895 | A | | 10/1999 | |
|---|---|---|---|---|---|
| EP | 1876607 | A1 | | 1/2008 | |
| EP | 2606491 | A1 | | 6/2013 | |
| JP | H11023508 | A | | 1/1999 | |
| JP | H1172453 | A | | 3/1999 | |
| JP | H11503231 | A | | 3/1999 | |
| JP | H11132978 | A | | 5/1999 | |
| JP | H-11264808 | A | * | 9/1999 | ............. G01N 27/12 |
| JP | H11264808 | A | | 9/1999 | |
| JP | 2002526769 | A | | 8/2002 | |
| JP | 2003307481 | A | | 10/2003 | |
| JP | 2006053059 | A | | 2/2006 | |
| JP | 2006306957 | A | | 11/2006 | |
| JP | 2013543013 | A | | 11/2013 | |
| WO | 9630750 | A1 | | 10/1996 | |
| WO | 0020852 | A1 | | 4/2000 | |
| WO | 2006117967 | A1 | | 11/2006 | |
| WO | 2012023992 | A1 | | 2/2012 | |

OTHER PUBLICATIONS

Dobbelin, et al.,"Influence of Ionic Liquids on the Electrical Conductivity and Morphology of PEDOT:PSS Films", American Chemical Society, 2007, 19, 2147-2149.

EP16865943.1 Communication Pursuant to Article 94(3) dated Aug. 12, 2020, 8 pgs.

EP16865943.1 Extended European Search Report dated Mar. 28, 2019; 12 pgs.

Freund, et al., A Chemically Diverse Conducting Polymer-Based "Electronic Nose", Proc. Natl. Acad. Sci. USA, 1995, vol. 92, p. 2652-2656.

Gupta, et al., Advances in Sensor Based on Conducting Polymers, Journal of Scientific Industrial Research, vol. 65, Jul. 2006, p. 549-557.

Ishida, et al., Improvement of Olfactory Video Camera: Gas/Odor Flow Visualization System, Sensors and Actuators B 83 (2002) 256-261, 6 pgs.

Kikuchi, et al., "Ammonia Gas Sensors with Conducting Polymers", IEICE Technical Report. OME, Organic Material Electronics, Aug. 15, 2001 (May 15, 2011), 101(253), p. 55-59.

Li, et al., Development of QCM Trimethylamine Sensor Based on Water Soluble Polyaniline, Sensors ISSN 1424-8220, Sensors 2007, 7, p. 2378-2388.

NIPPON TELEGR & TELEPH CORPARB001 From Client Dec. 14, 2020Feb 23, 2006This is a Foreign ReferenceJP.

Pandey, et al., A Review of Sensor-Based Methods for Monitoring Hydrogen Sulfide. Trends Anal Chem, ResearchGate, TRAC Trends in Analytical Chemistry, vol. 32, Feb. 2012, p. 87-99.

PCT/JP2015/082326 International Search Report dated Feb. 23, 2016; 2 pgs.

PCT/JP2016/055082 International Search Report dated Jun. 7, 2016; 2 pgs.

Souza, et al., Polypyrrole Based Aroma Sensor, Elsevier, Synthetic Metals 102 (1999) p. 1296-1299.

Tokuhiro, et al., "Study of Gas/Ordor Flow Visualization System Using Array of Miniaturized QCM Gas Sensors", IEICE Technical Report, May 1999, OME99-21, p. 53-58.

Tonosaki, Identity of "Odor" and "Scent", "Nioi" to "Kaori" no Shoutai, (True Nature of 'Odor' and Fragrance), p. 69, 1.6-10.

Touhara, Fragrance and Deliciousness: Olfactory Research in Food Science, Kagaku to Seibutsu (Chemistry and Biology), vol. 45, No. 8, 2007.

EP16865943.1 Office Action dated Aug. 30, 2022, 5 pgs.

* cited by examiner

| DOPANT TYPE | EXAMPLES |
|---|---|
| INORGANIC ANIONS | CHLORIDE ION, OXYCHLORIDE ION, BROMIDE ION, SULFATE ION, NITRATE ION, OR BORATE ION |
| ORGANIC ANIONS | ALKYL SULFONATES, BENZENE SULFONATES, OR CARBOXYLATES |
| POLYMERIC ACID ANIONS | SULFONATES, POLYMERIC PHOSPHORIC ACID COMPOUNDS, POLYMERIC BORIC ACID COMPOUNDS, POLYMERIC NITRIC ACID COMPOUNDS, POLYMERIC ALUMINIC ACID COMPOUNDS, POLYMERIC TITANIC ACID COMPOUNDS, POLYMERIC HALOGEN ACID COMPOUNDS AND DERIVATIVE ACIDS THEREOF, OR POLYSTYRENE SULFONATES |
| IONIC LIQUIDS | PYRIDINE-BASED, ALICYCLIC AMINE-BASED, OR ALIPHATIC AMINE-BASED IONIC LIQUID |

FIG. 3

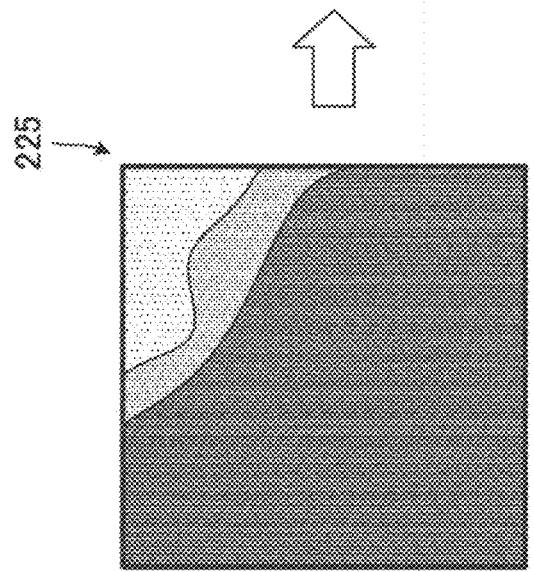
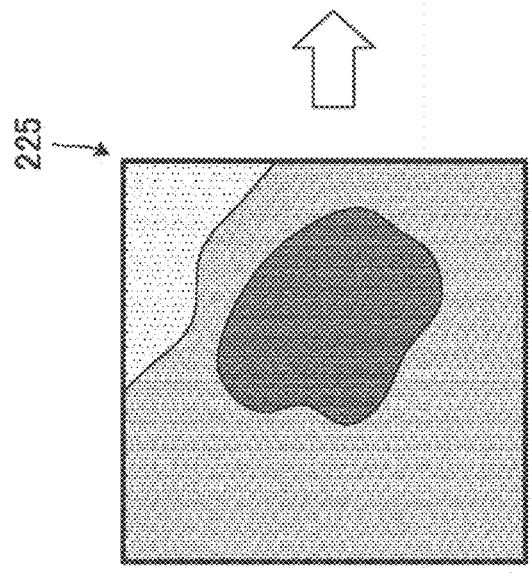
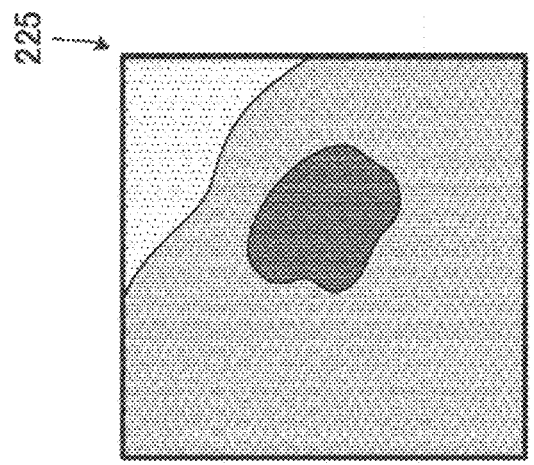
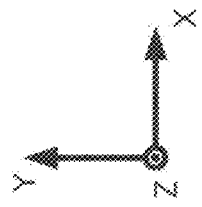
FIG. 7

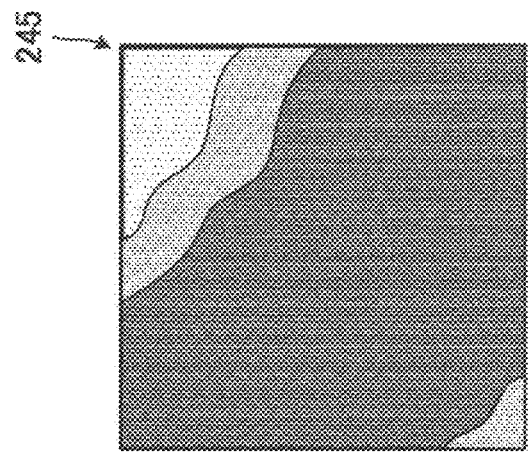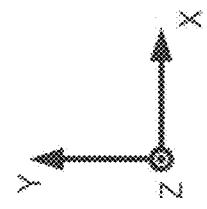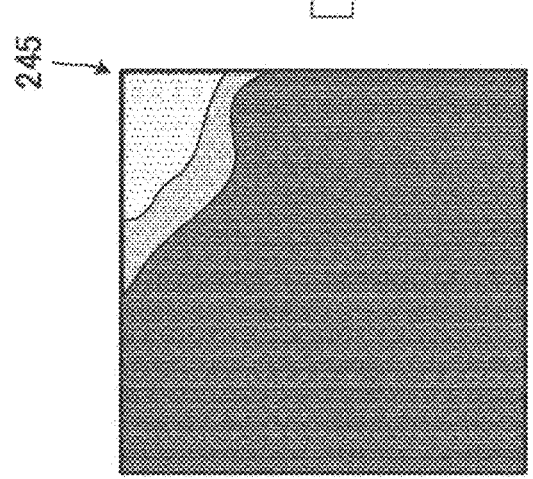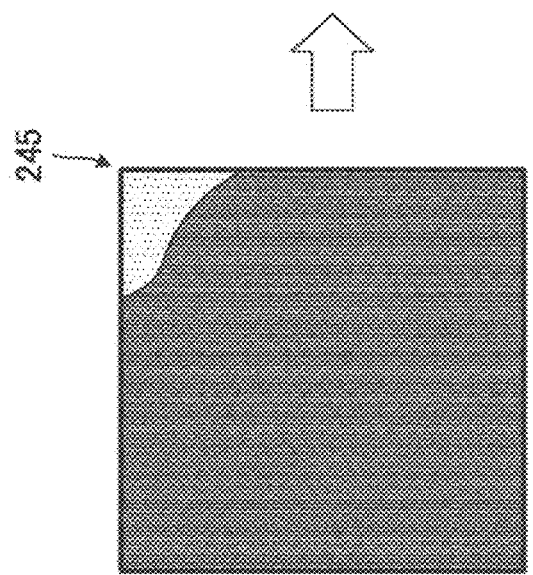
FIG. 9

ODOR SENSOR AND ODOR MEASUREMENT SYSTEM

CROSS-REFERENCE TO RELATED APPLICATION

This application is a continuation application of U.S. patent application Ser. No. 15/982,699, filed on May 17, 2018, entitled "ODOR SENSOR AND ODOR MEASUREMENT SYSTEM," which is a continuation application of International Application No. PCT/JP2016/055082, filed Feb. 22, 2016, which claims priority to PCT/JP2015/082326, filed Nov. 17, 2015. The contents of these applications are incorporated herein by reference in their entirety.

BACKGROUND

Field

Embodiments relate to a substance absorbing membrane, and an odor sensor which includes the adsorbent membrane. Moreover, embodiments relate to an odor measuring system which includes the odor sensor.

Description of the Related Art

An odor is the only sense, among the senses possessed by a human being, which is not mechanically measurable by a sensor, and it is anticipated that the information expected to be provided by the odor data can be utilized in various aspects such as medicine, safety, security, environment, EC (e-commerce), and IoT (Internet of Things).

The history of odor sensors goes back up to the example of using canaries as sensors in coal mines. It was the first time to practically use a catalytic combustion type inflammable gas detector intended for detecting inflammable gases generated in coal mines and the like in the 1920's.

Thereafter, it came to be known in the period from the 1930's to the 1950's that when metal oxide semiconductors are brought into contact with various gases, the electrical conductivities of the semiconductors change. Sensors utilizing this phenomenon as gas sensors were first put to practical use in Japan by Taguchi et al., in 1962.

Since then, the range of the type of the metal oxide that are utilized in semiconductor gas sensors have been heretofore extended to $SnO_2$, $ZnO$, $In_2O_3$, $WO_3$, $V_2O_3$, and the like. Furthermore, studies have been conducted to increase sensitivity or to impart gas selectivity to the metal oxides by adding Pd, Pt, Au, Ag, or the like to these oxides, by regulating the shape of the elements, or the like, and thus those semiconductor gas sensors have been utilized in various settings.

In recent years, the range of gases used as the targets of detection has been expanded from inflammable gases to ozone, halogenated gases including fluorine and chlorine, hydrogen sulfide, and non-specific mixed gases generated from foul odors such as fire and mouth odor.

However, such a sensor basically performs measurement of odors by combining sensors that respectively respond to known specific gases, and it has been difficult to implement the expression of actual odors, which originate from substances that are not well-known or from an interaction of a plurality of substances.

Among these attempts, sensors having an array structure composed of a plurality of sensors that use electroconductive polymers such as polypyrrole were suggested in the 1990's, and thus, techniques of expressing odors by mapping the differences in the responses of sensors in an array form have been investigated and put to practical use.

For example, Souza, et al. published a method of expressing an odor by using a polypyrrole thin film formed on a four-terminal gold electrode using five kinds of dopants such as p-toluene sulfonic acid, as a gas absorbent membrane, and mapping any changes in the oxidation reduction potential of the membrane caused by gas adsorption (Non-Patent Literature 1: Synthetic Metals 102 (1999) 1296-1299 <http://www.cin.ufpe.br/~tbl/artigos/synthetic-metals102.pdf>).

Freund, et al. suggested a method of visualizing an odor by incorporating a substance that serves as a plasticizer (polystyrene or a derivative thereof) when polypyrrole is polymerized, thereby changing the film properties, configuring a capacitor array using this membrane as a resistive film, and mapping the change in capacity occurring when a gas is adsorbed to this capacitor array (Non-Patent Literature 2: Proc. Nat'l. Acad. Sci. USA, Vol. 92, pp. 2652-2656, March 1995 <http://www.pnas.org/content/92/7/2652.full.pdf>).

Sensors that use electroconductive polymers have been considered to have a possibility of being appropriate as sensors for gas measurement, and studies have been conducted thereon. There is known a sensor having a structure in which polypyrrole or polyaniline is used as an electroconductive polymer, the oxidation-reduction state of the electroconductive polymer is controlled in advance to a specified value, and then the changes in the surface potential caused by adsorption of various gases are read out (Non-Patent Literature 3: Journal of Scientific & Industrial Research, Vol. 65, July 2006, pp. 549-557<http://nopr.niscair.res.in/bitstream/123456789/4862/1/JSIR%2065(7)%20549-557.pdf?utm_source=The_Journal_Database&trk=right_banner&id=1405260546&ref=a9e18615352a09d89724ffaafef1cd18>). However, the sensor investigated in this study cannot be said to be a sensor with high sensitivity, while it has linearity in sensitivity at a high concentration range.

Pandy, et al. reported that hydrogen sulfide could be detected with high sensitivity by using an electrode produced by forming nanowires of polyaniline on gold nanoparticles or an electrode produced by forming nanowires of polyaniline on a metal salt, and reading out any impedance changes caused by gas adsorption onto those electrodes (Non-Patent Literature 4: Trends in Analytical Chemistry, Vol. 32, 2012, pp. 87-99 <http://www.researchgate.net/profile/Ki_Hyun_Kim4/publication/228073634_A_review_of_sensor-based_methods_for_monitoring_hydrogen_sulfide/links/09e414fec247ccc0fa000000.pdf>).

Li, et al. have investigated on the adsorption characteristics of triethylamine, ethanol, and ethyl acetate by producing a prototype of a polyaniline-coated QCM by coating a QCM by dropping water-soluble polyaniline thereon. It was found that a polyaniline-coated QCM shows responses with satisfactory reproducibility, and shows different responses depending on the polarity of the adsorbed gas (Non-Patent Literature 5: Sensors, 2007, 7(10), 2378-2388<http://www.mdpi.com/1424-8220/7/10/2378/htm>).

Nathan, et al. suggested an array type odor sensor comprising a QCM, a metal oxide semiconductor, an optical sensor, a MEMS sensor, an electrochemical sensor, or the like, the array type odor sensor being obtained by forming at least one kind or more of electroconductive polymers such as polypyrrole, polyaniline, and polythiophene (Patent Document 1: U.S. Pat. No. 6,631,333 B1). Such a method has made a success in showing the patterns of a sensor array disposed in a matrix form by such a method, by utilizing the fact that various electroconductive polymers have different gas adsorption states due to the differences in the surface properties of the electroconductive polymers.

Meanwhile, regarding the number of human olfactory receptors, it is considered that there are about 380 kinds of olfactory receptors (Non-Patent Literature 6: Kagaku to Seibutsu (Chemistry and Biology), Vol. 45, No. 8, 2007). From this, it is speculated that in order to perform an accurate odor pattern analysis that is close as far as possible to the odor pattern analysis system of the human being, 30 to 40 kinds of sensor arrays at the minimum are desired.

As means for such sensor arrays, Nathan et al. as described above have suggested to use five kinds of electroconductive polymers and derivatives thereof in adsorbent membranes, and thus, numerous adsorbent membranes can be prepared when various derivatives of electroconductive polymers and the like having alkyl substituents are used.

Generally, the mechanism of olfactory perception of the nose of animals including human being can be explained as follows.

First, when an odor substance enters into the nose, the odor substance dissolves into a special mucous membrane called olfactory epithelium at the top part of the nasal cavity and is perceived there. Then, the olfactory cells in the olfactory epithelium generate electric signals, the electric signals are transmitted through the olfactory nerves and olfactory bulbs to the brain (limbic system), and the sense of odor occurs.

Here, in the olfactory cilia spread over the mucosal layer of the olfactory epithelium, olfactory receptors (odor sensors) that catch odors exist. Several olfactory receptors respond to one odor molecule, and thus an odor is detected. Furthermore, when the concentration of an odor changes, the combination of the responding olfactory receptors is changed, and the odor is perceived as a different odor.

Tonosaki wrote in his book that attention has been paid to a plurality of odor causative substances having different molecular structures produce similar odors, and that at least some parts of the external form of those molecules giving similar odors resemble very closely has been found in a study by Amoore. That is, it has been suggested thereby that there is a possibility that olfactory receptors may have recognized the outline structures of the molecules.

In a different study, it was explained that these olfactory receptors recognize the respective frequencies produced by various odor causative substances (Non-Patent Literature 7: TONOSAKI, Keiichi, "'Nioi' to 'Kaori' no Shotai (True Nature of 'Odor' and 'Fragrance')").

As such, it has been considered that explanations can be provided more easily by thinking that, among the properties possessed by an odor causative substance, olfactory receptors detect not those relatively direct information by which a compound can be identified, such as the molecular weight, the oxidation reduction potential, a functional group and the position of bonding thereof, which have been used in chemical analyses hitherto; but those indirect characteristics of a substance, such as the external form of a molecule.

However, even in the case of using the above-described technologies, it is not yet sufficient to provide a sensor that is satisfactory for accurately detecting complicated odor pattern.

Furthermore, in a case in which these derivatives necessary for sensing are synthesized, many compounds should be derivatized in the monomer stage, and then the derivatives should be polymerized to obtain polymers. However, the method described above would not synthesize electroconductive polymers having all kinds of physical properties.

Therefore, the range of differences in the physical properties of the adsorbent membrane should be narrowed.

SUMMARY

Embodiments have been made in view of the above-described problems. Embodiments provide an odor sensor that enables detection and rigorous distinction of a particular odor from a complicated collection of odors, like in the human olfactory perception; a substance adsorbing membrane used in the odor sensor; and a method for producing the substance adsorbing membrane. A database of odor patterns can be established by using such a sensor, and the database can be utilized in odor identification.

According to at least one embodiment, there is provided a method for producing a substance adsorbing membrane by significantly widening the scope of characteristics of the substance adsorbing membrane, and thereby enabling an increase in the number of elements of sensor arrays.

As a result, embodiments demonstrate that, when an electroconductive polymer is used as a basic skeleton of a substance adsorbing membrane, and a salt or an acid which forms a co-ion having a counterion of the electroconductive polymer or a dopant as a cation is incorporated to co-exist with the electroconductive polymer, the physical properties (polarity, hydrophilicity/hydrophobicity, steric hindrance, and the like) of the electroconductive polymer basic skeleton are significantly changed, and substantially limitless kinds of substance adsorbing membranes can be configured. Thus, the inventors finally completed the present invention.

Accordingly, embodiments provide the following means in order to solve the problems described above.

According to at least one embodiment, there is provided an odor sensor including two or more sensor elements each having a substance adsorbing membrane for adsorbing odor substances; and a signal conversion unit for determining the state of adsorption of the odor substance to the substance adsorbing membrane, in which the substance adsorbing membrane has an electroconductive polymer and a dopant capable of changing the substance characteristics of the electroconductive polymer, the substance adsorbing membranes included in the two or more sensor elements have respectively different content ratios of the dopant with respect to the electroconductive polymer. The signal conversion unit is configured to detect a change in oscillation frequency of the substance adsorbing membrane due to the adsorption of the substance thereto.

According to at least one embodiment, when an odor substance is adsorbed to the substance adsorbing membrane, the characteristics of the substance adsorbing membrane change, and the physical, chemical, or electrical characteristics and the like of the substance adsorbing membrane are changed. When this change in the characteristics of the substance adsorbing membrane is detected and amplified by the signal conversion unit, the individual sensor elements can measure the state of adsorption of the odor substance to the substance adsorbing membrane.

According to at least one embodiment, the adsorption characteristics of the substance adsorbing membrane for an odor substance can be changed by means of the type of the electroconductive polymer included in the substance adsorbing membrane, and the type and the amount of addition of the dopant added to the electroconductive polymer. To a substance adsorbing membrane having particular adsorption characteristics, a plurality of odor substances having an affinity to the adsorption characteristics can be adsorbed. A gas generally includes a large number of odor substances that constitute an "odor", and the collection of odor substances included in a gas has a variable amount of adsorption to a certain substance adsorbing membrane depending on the composition of the collection.

Since an odor sensor includes two or more sensor elements each including a substance adsorbing membrane having respectively different dopant content ratios, the odor sensor can detect two or more states of adsorption for a single gas. That is, the odor sensor can output detection patterns originating from the states of adsorption to be respectively measured by the two or more sensor elements.

The term "odor substance" according to various embodiments means, in a broad sense, a substance capable of adsorbing to a substance adsorbing membrane. Therefore, substances that are generally not considered as odor causative substances can also be included. In many cases, the "odor" includes a plurality of causative odor substances, and substances that are not recognized as odor substances. Moreover, unknown odor substances may also exist. The various embodiments have paid attention not to the adsorption of those individual odor substances, but to the amount of adsorption of odor substances having particular adsorption characteristics, which can be adsorbed to a particular substance adsorbing membrane. Meanwhile, according to various embodiments, even in a case in which the words "odor substance" is simply described, the term may mean, not individual odor substances, but a "collection of odor substances" which may include a plurality of odor substances.

According to at least one embodiment, the signal conversion unit determines the state of adsorption by measuring any changes in the physical, chemical, or electrical characteristics of the substance adsorbing membrane, the changes being attributed to adsorption of the odor substance to the substance adsorbing membrane.

According to at least one embodiment, the signal conversion unit expresses the state of adsorption of odor substances as electronic data which can be data processed by a computer or the like, by measuring any changes in the physical, chemical, or electrical characteristics of the substance adsorbing membrane, and converting the measurement results to electric signals.

According to at least one embodiment, the electroconductive polymer includes a π-electron conjugated polymer.

According to at least one embodiment, the π-electron conjugated polymer is selected from the group consisting of polypyrrole and derivatives thereof, polyaniline and derivatives thereof, polythiophene and derivatives thereof, polyacetylene and derivatives thereof, and polyazulene and derivatives thereof.

When such a π-electron conjugated polymer is used as an electroconductive polymer, control of the adsorption characteristics by various dopants is made easier.

According to at least one embodiment, the adsorption characteristics of the substance adsorbing membrane are changed by the dopant.

According to at least one embodiment, the dopant is an inorganic ion.

According to at least one embodiment, the inorganic ion is selected from the group consisting of chloride ion, oxychloride ion, bromide ion, sulfate ion, nitrate ion, and borate ion.

According to at least one embodiment, the dopant is an organic acid anion.

According to at least one embodiment, the organic acid anion is selected from the group consisting of an alkyl sulfonate, benzenesulfonate, and a carboxylate.

According to at least one embodiment, the dopant is a polymeric acid anion.

According to at least one embodiment, the polymeric acid anion is polyacrylate or polystyrene sulfonate.

According to at least one embodiment, the dopant is a salt.

According to at least one embodiment, the dopant is an ionic liquid.

According to at least one embodiment, the ionic liquid is a pyridine-based, alicyclic amine-based, or aliphatic amine-based ionic liquid.

According to at least one embodiment, by using the inorganic ion, organic acid anion, polymeric acid anion, salt, ionic liquid, and the like as the dopant, the adsorption characteristics of the substance adsorbing membrane can be arbitrarily controlled.

According to at least one embodiment, there is provided an odor sensor arrangement structure including two or more arranged odor sensors each including a sensor element, each of the odor sensors including two or more of the sensor elements, each of the odor sensors having a substance adsorbing membrane for adsorbing the odor substances; and a signal conversion unit for determining the state of adsorption of the odor substance to the substance adsorbing membrane, in which the substance adsorbing membrane has an electroconductive polymer and a dopant capable of changing the substance characteristics of the electroconductive polymer, and the respective substance adsorbing membranes included in the two or more sensor elements have different content ratios of the dopant with respect to the electroconductive polymer. The signal conversion unit is configured to detect a change in oscillation frequency of the substance adsorbing membrane due to the adsorption of the substance thereto Since two or more odor sensors are arranged, the state of adsorption of an odor substance at two or more distinct positions can be detected, and therefore, the positional information of the odor substance or a gas including the odor substance can be detected.

According to at least one embodiment, the direction in which the odor substance has approached to the odor sensors, based on the differences in the amount of adsorption of the odor substance at the respective odor sensors is detected by the two or more arranged odor sensors.

Since the amounts of adsorption of an odor substance to a substance adsorbing membrane at two or more different positions can be measured, the direction of movement of the odor substance or a gas including the odor substance can be figured out based on the difference in the amount of adsorption of the odor substance. That is, the direction of movement of an odor substance can be detected.

According to at least one embodiment, the two or more odor sensors respectively have the same combination of substance adsorbing membranes.

When two or more arranged odor sensors respectively have a substance adsorbing membrane of the same combination, it is possible to detect an odor substance using odor sensors of the same configuration at separate places. Therefore, even there is a plurality of odor substances or a plurality of gases including the odor substances, those substances or gases can be discriminated, and also, the direction of movement of those substances or gases can be detected.

According to at least one embodiment, the arrangement of the sensor elements is the same in each of the two or more odor sensors.

When two or more arranged odor sensors respectively have the same arrangement, production of the odor sensor arrangement structure is facilitated. Furthermore, particularly in a case in which a large-sized odor sensor arrangement structure is produced, even if defects or lacks occurs in some part of the odor sensor arrangement structure, restoration is facilitated.

According to at least one embodiment, the two or more sensor elements are planarly arranged, and the two or more odor sensors are planarly arranged.

Since the various sensor elements are planarly arranged, and the various odor sensors are planarly arranged, the overall shape of the odor sensor arrangement structure can be made into a planar shape. When the overall shape of the odor sensor arrangement structure is a planar shape, installation of the odor sensor arrangement structure at any arbitrary planar-shaped place such as the wall, the ceiling, or the floor is made easier.

According to at least one embodiment, there is provided an odor measurement system including a detection unit having an odor sensor, the odor sensor including two or more sensor elements capable of interacting with an odor substance; a data processing unit for patterning the electrical characteristics based on an interaction between the sensor elements and the odor substance, and visualizing the pattern; and an analysis unit for analyzing and recognizing the pattern, in which the odor sensor includes two or more sensor elements each having a substance adsorbing membrane for adsorbing the odor substances; and a signal conversion unit for determining the state of adsorption of the odor substance to the substance adsorbing membrane, the substance adsorbing membrane has an electroconductive polymer and a dopant capable of changing the substance characteristics of the electroconductive polymer, and the respective substance adsorbing membranes included in the two or more sensor elements have respectively different content ratios of the dopant with respect to the electroconductive polymer. The signal conversion unit is configured to detect a change in oscillation frequency of the substance adsorbing membrane due to the adsorption of the substance thereto.

Since the sensor element and the sensor of the present invention can be provided with a wide variety of substance adsorbing membranes having physical, chemical, or electrical characteristics specific to odor substance, the sensor element and the sensor can detect an odor even in a general environment in which various substances exist as a mixture, without limiting the substance.

Furthermore, such a sensor of the present invention is different from conventional odor sensors which are based on the principle of gas analysis, from the viewpoint that the sensor of the invention does not express an odor as components of constituent substances but outputs an image pattern of an odor.

BRIEF DESCRIPTION OF THE DRAWINGS

FIG. 3 shows examples of compounds which can be used as dopants for the odor sensor according to an embodiment.

FIG. 7 is an explanatory diagram illustrating the changes in the state of adsorption occurring when water is desorbed from a substance adsorbing membrane.

FIG. 9 is an explanatory diagram illustrating the changes in the state of adsorption occurring when Japanese sake is desorbed from a substance adsorbing membrane.

DETAILED DESCRIPTION

Figure 1:
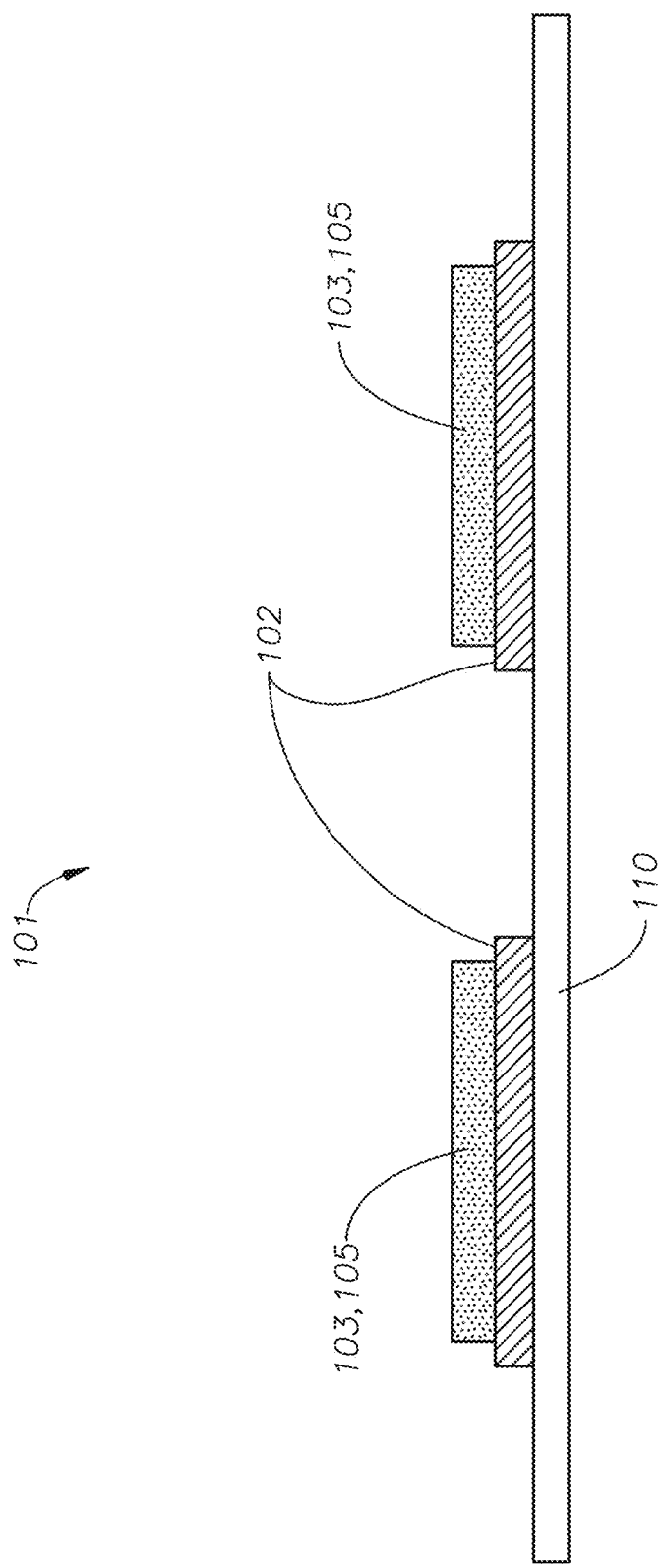
FIG. 1 is a cross-sectional view of a sensor element of an odor sensor according to an embodiment.

According to at least one embodiment, there is provided an odor sensor, including at least two sensor elements each including a substance adsorbing membrane which adsorbs at least one or more odor substances included in the air; and a signal conversion unit which measures the physical, chemical, or electrical characteristics of the substance adsorbing membrane after adsorption of the above-mentioned substance, in which the substance adsorbing membrane contains an electroconductive polymer and a dopant capable of modifying the substance characteristics of the electroconductive polymer, and the at least two sensor elements are respectively provided with substance adsorbing membranes having different basic skeletons and proportions of the dopant.

According to at least one embodiment, the substance adsorbing membrane can modify the membrane characteristics by means of the dopant, and each substance adsorbing membrane selectively and specifically adsorbs a certain substance. Thereby, any changes in the physical, chemical, or electrical characteristics caused by the substance adsorbed to the surface of the substance adsorbing membrane can be detected, and therefore, the state of adsorption of the substance can be measured based on the changes.

Herein, an "odor" includes a collection of specific single molecules or molecular groups consisting of different molecules each at different concentrations and which can be acquired as olfactory information by human beings or living beings including human beings.

According to at least one embodiment, the signal conversion unit measures the state of adsorption of an odor substance to a substance adsorbing membrane, and measures any changes in the physical, chemical, or electrical characteristics of the substance adsorbing membrane caused by adsorption of the odor substance to the substance adsorbing membrane. Here, the "state of adsorption of an odor substance to a substance adsorbing membrane" conceptually includes, for example, an "amount of adsorption of an odor substance to a substance adsorbing membrane". Due to an increase or decrease in the amount of adsorption of an odor substance to a substance adsorbing membrane, the physical, chemical, or electrical characteristics of the substance adsorbing membrane change, and the state of adsorption of the odor substance to the substance adsorbing membrane is determined by measuring the quantity of the changes. Furthermore, specific examples of the "physical, chemical, or electrical characteristics" include physical characteristics such as changes in the frequency of a quartz crystal oscillator, changes in the optical characteristics (changes in the absorption wavelength, changes in the absorbance, changes in the refractive index, and the like), and changes in the velocity of the surface acoustic waves; electrochemical characteristics such as changes in the electrochemical impedance and changes in the oxidation reduction potential; and electrical characteristics such as charge coupling, gate voltage, impedance, resonance frequency, and band gap.

<Sensor Element>

Hereinafter, a sensor element is explained with reference to the drawings.

FIG. 1 is a cross-sectional view of a sensor element 101 according to an embodiment. The sensor element 101 is provided on the surface with a sensor main body 102; and a substance adsorbing membrane 103 that is provided on the surface of the sensor main body 102 and adsorbs an odor substance (chemical substance). In FIG. 1 as an example of the overall configuration, the sensor main body 102 is provided on a substrate 110. Furthermore, for example, a configuration in which an excitation electrode (not illustrated in the diagram) is disposed on the surface on the opposite side may also be adopted.

According to at least one embodiment, the substance adsorbing membrane 103 is a thin film formed from a π-electron conjugated polymer, and this π-electron conjugated polymer thin film can contain at least one kind selected from an inorganic acid, an organic acid, and an ionic liquid as a dopant 105.

According to at least one embodiment, the sensor main body 102 is provided so as to have a function as a signal conversion unit (transducer) which measures the state of adsorption of a substance by measuring any changes in the physical, chemical, or electrical characteristics caused by the substance adsorbed to the surface of the substance adsorbing membrane. The physical, chemical, or electrical element of the sensor main body is not particularly limited as long as the element is a sensor, such as a quartz crystal oscillator sensor (QCM), a surface acoustic wave sensor, a field effect transistor (FET) sensor, a charge coupled element sensor, a MOS field effect transistor sensor, a metal oxide semiconductor sensor, an organic electroconductive polymer sensor, or an electrochemical sensor, and various sensors can be used as appropriate according to the purpose from case to case.

The structure of the element can adopt various different structures according to the purpose of detection of the sensor. For example, in the case of a quartz crystal oscillator, the sensor may have a structure of a conventional type in which electrodes are attached on both surfaces, or a sensor having a structure having a separated electrode with only a single-sided electrode, by which a high Q value can be acquired, may also be used.

According to at least one embodiment, the π-electron conjugated polymer used as the substance adsorbing membrane 103 is not particularly limited; although, a polymer having a so-called π-electron conjugated polymer, such as polypyrrole or a derivative thereof, polyaniline or a derivative thereof, polythiophene or a derivative thereof, polyacetylene or a derivative thereof, or polyazulene or a derivative thereof as a skeleton, is favorable.

Usually, such a π-electron conjugated polymer exhibits electrical conductivity such that the skeletal polymer itself becomes a cation in an oxidized state, and the polymer includes an anion as a dopant. Meanwhile, in accordance with at least one embodiment, a neutral π-electron conjugated polymer which does not have a dopant can also be selected as the substance adsorbing membrane.

Figure 2:
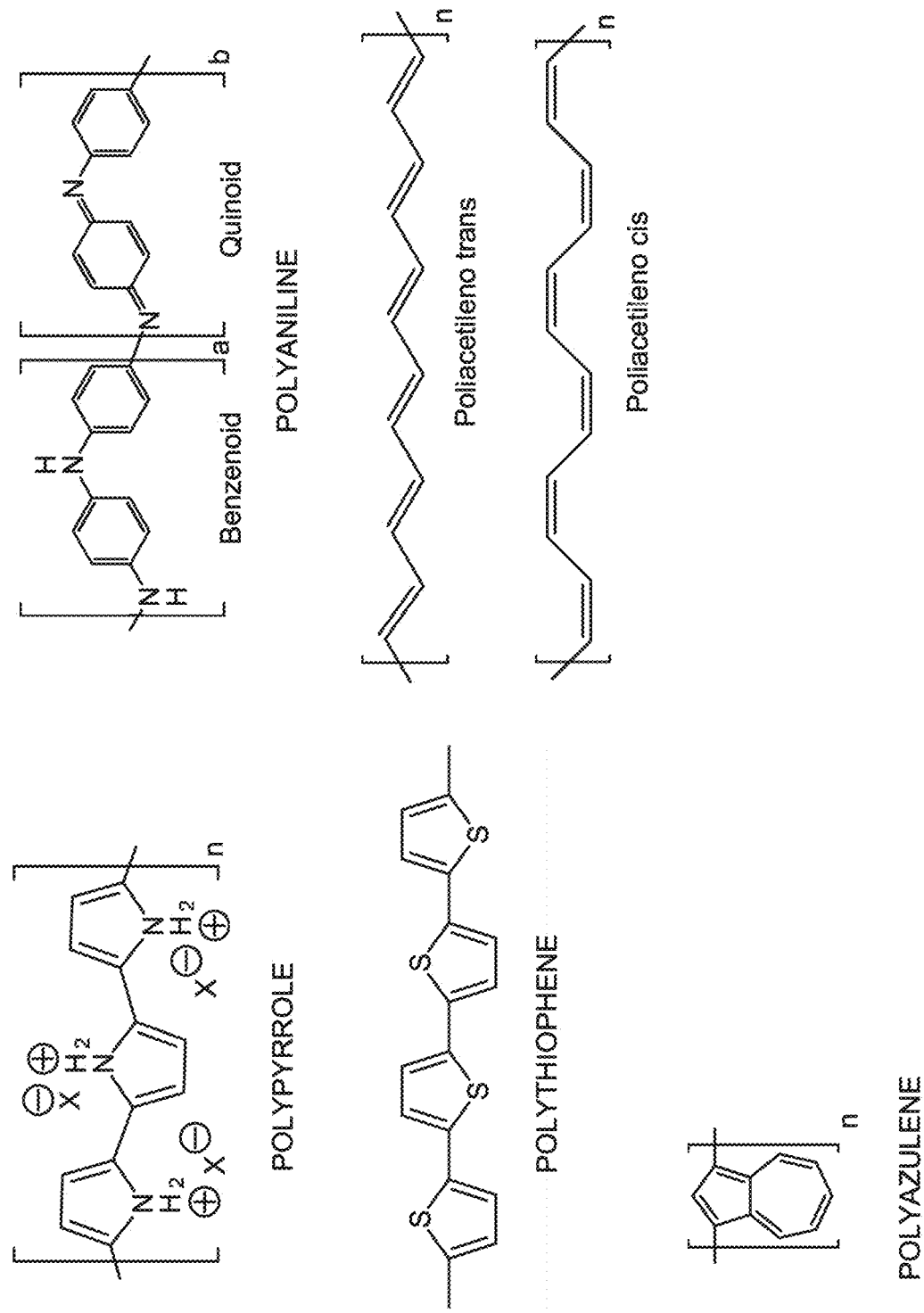
FIG. 2 shows examples of π-electron conjugated polymers which can be used according to an embodiment.

In the case of using an electrically conductive π-electron conjugated polymer having a dopant, it is possible to use various substances as the dopant. FIG. 2 and FIG. 3 illustrate some examples of substances which can be used in chemical formulae and a table.

According to at least one embodiment, examples of the dopant include inorganic ions such as chloride ion, oxychloride ion, bromide ion, sulfate ion, nitrate ion, and borate ion; organic acid anions such as alkyl sulfonates, benzenesulfonates, and carboxylates; and polymeric acid anions such as polyacrylates and polystyrene sulfonates.

Furthermore, in addition to the direct conjugate of anions as described above, a method of incorporating a salt such as table salt, or an ionic compound which includes both cations and anions, such as an ionic liquid, into a neutral π-electron conjugated polymer and thereby performing doping under chemical equilibrium, can also be used.

According to at least one embodiment, the ionic liquid which can be used herein is not particularly limited; although, examples thereof include, based on the type of the cation, pyridine-based, alicyclic amine-based, and aliphatic amine-based ionic liquids. By selecting the type of the anion to be used in combination with this, various structures can be synthesized.

According to at least one embodiment, examples of the cation include ammonium-based ions such as imidazolium salts and pyridinium salts; phosphonium-based ions; and inorganic ions.

According to at least one embodiment, examples of the anion to be employed include halogen-based ions such as bromide ion and triflate; boron-based ions such as tetraphenylborate; and phosphorus-based ions such as hexafluorophosphate.

According to at least one embodiment, the content of the dopant in the π-electron conjugated polymer may be adjusted to the range of 0.01 to 5, and preferably to the range of 0.1 to 2, in a case in which a state of having one molecule of the dopant incorporated into two repeating units which form the high dopant is designated as 1. When the content is lower than or equal to the minimum value of this range, the characteristics of the membrane are lost, and when the dopant is incorporated in an amount more than or equal to the maximum value, the effect of adsorption characteristics possessed by the polymer itself disappears, and it also becomes difficult to produce a membrane having desired adsorption characteristics in a well-controlled manner. Also, since a membrane in which the dopant, which is a low molecular weight substance, is predominant is usually obtained, durability of the membrane is deteriorated to a large extent. Therefore, when the content of the dopant is in the range mentioned above, the detection sensitivity for the chemical substance as an odor substance can be maintained at a suitable level.

According to at least one embodiment, the thickness of the substance adsorbing membrane can be selected as appropriate according to the characteristics of the substance which serves as an object of adsorption. For example, the thickness can be adjusted to the range of 10 nm to 10 μm, and preferably, it is preferable to adjust the thickness to 50 nm to 800 nm. When the membrane thickness is less than 10 nm, a sufficient sensitivity cannot be obtained. Furthermore, when the membrane thickness is more than 10 μm, the weight of the membrane exceeds the upper limit of the weight that can be measured by the sensor element, which is not preferable.

<Method for Producing Substance Adsorbing Membrane>

Regarding a method for producing the substance adsorbing membrane 103, for example, the membrane can be produced by selecting an appropriate membrane forming method, such as diluting a solvent stock solution with various solvents, subsequently dissolving the dopant component therein to prepare a membrane solution, and then dropping the membrane solution on the surface of a sensor element using a microdispenser or the like. For the production of the substance adsorbing membrane 103, application of the membrane solution by ink jetting can also be employed.

<Sensor>

Next, the sensor as a whole is explained.

Figure 4:
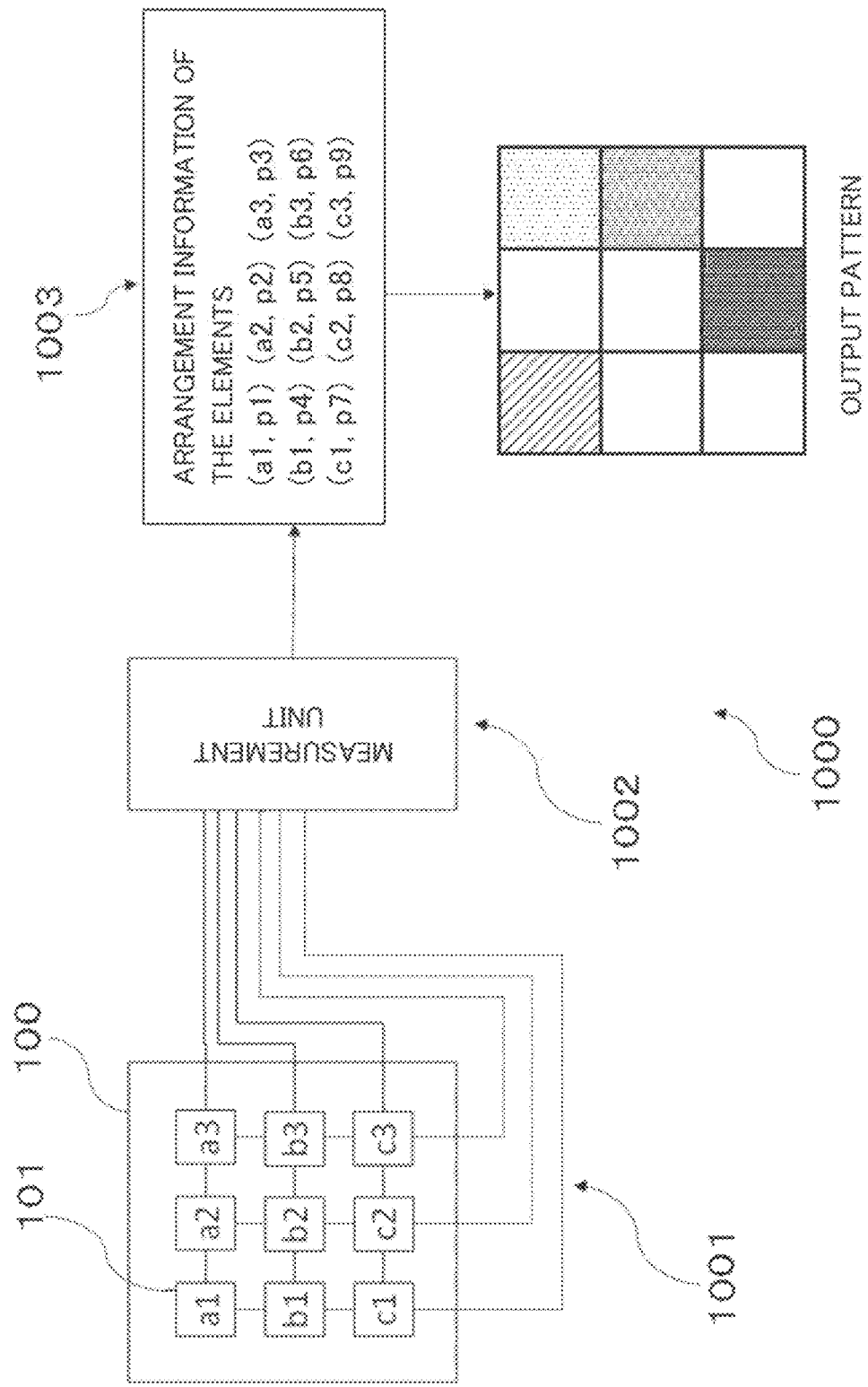
FIG. 4 is a schematic diagram of an odor measurement system according to an embodiment.

FIG. 4 is a schematic diagram of an odor sensor 100 and an odor measurement system 1000 according to an embodiment, which are described below. The odor sensor 100 includes sensor elements 101 as described above.

Since the odor sensor 100 according to an embodiment has a plurality of the sensor elements 101, the odor sensor 100 is enabled to adsorb substances having various characteristics by varying, for example, the configuration of the substance adsorbing membranes 103 provided on the surface of the sensor elements 101 for every element. The combination of the elements can be modified in various ways according to the purpose of the detection. Substance recognition patterning as a whole is performed by detecting the adsorption pattern of each substance, and thereby, an adsorption pattern related to a certain group of odor substances can be presented.

In the conventional so-called odor sensor, most of the sensors have single probes for detecting odor causative substance molecules, and in such a case, only a qualitative or quantitative measurement of the single odor substance molecules can be performed.

In contrast, the odor sensor according to an embodiment is provided with a plurality of sensor elements. Furthermore, a configuration of exhibiting a reaction specific to a molecule to which the action of the sensor is directed can be adopted for each sensor, by providing substance adsorbing membranes having respectively different characteristics on the surface of the sensor element, and the extents of the action directed to the respective intended molecules can be regulated.

Here, it is also possible that all of the sensor elements used herein can have an identical element structure, that is, in the case of a QCM detection system, the sensor elements can form an array structure composed only of QCM sensors, and in the case of a FET detection system, the sensor elements can form a sensor element array structure composed only of FET sensors. Alternatively, an element array may also be configured by having a plurality of types of the element structures described above arranged together.

Meanwhile, regarding the π-electron conjugated polymer used as the substance adsorbing membrane 103, an array structure formed from a single membrane may be adopted, and a sensor array in which only the dopant is varied for each of the elements may be produced. Alternatively, a configuration in which the π-electron conjugated polymer itself may be varied for each of the elements, may also be adopted. Even in the latter case, the dopant can be optionally disposed on a sensor array, independently of the π-electron conjugated polymer.

On the occasion of configuring such a sensor array, the structure may be an array structure in which the substance adsorbing membrane is not formed in one or more of the sensor elements. These elements that do not have a membrane formed thereon can be used as references, and therefore, high detection accuracy can be secured.

As such, since the odor sensor according to an embodiment can use various combinations of the configuration of the sensor element main body and the substance adsorbing membrane, a variety of sensor configurations can be adopted according to the characteristics of the substance as an object of detection.

Sensor elements having different substance adsorbing membranes 103 applied thereon exhibit different interactions with an odor causative substance, which is an object of measurement. By disposing these sensors provided with different substance adsorbing membranes in an array form, changes in the frequency of the respective sensor elements can be detected and analyzed, and thus the causative factor of an odor can be analyzed qualitatively and quantitatively.

For example, more specifically, regarding the rules of arrangement of various sensor elements having different substance adsorbing membranes disposed on a substrate, the information of sensor arrangement about which sensor adsorbs and detects which odor substance as the information about the X-axis direction and the Y-axis direction, and a qualitative odor pattern formed by changes in frequency in the same element group (adsorption characteristics or the extent of interaction) expressed at least in three-dimensions, can be obtained.

According to at least one embodiment, the sensor element or the excitation electrode can be formed from any arbitrary electroconductive material. Examples thereof include inorganic materials such as gold, silver, platinum, chromium, titanium, aluminum, nickel, nickel-based alloys, silicon, carbon, and carbon nanotubes; and organic materials, including electroconductive polymers such as polypyrrole and polyaniline.

For example, when a functionally gradient membrane in which a slight gradient is made in the intensity of hydrophobicity, hydrophilicity or the like by the concentration distribution or chemical modification in the direction of spatial axes is used, the various sensors that constitute various arrays can have respectively slightly different interactions with an odor causative substance, which is a substance to be measured.

In addition to that, the influence exerted by other coexisting oscillators, that is, crosstalk can be reduced by changing the resonance frequencies of various oscillators, which is preferable. The odor sensor can be arbitrarily designed such that various oscillators within a common substrate show different sensitivities.

In a case in which the resonance frequencies of various quartz crystal oscillators are the same, attempts have been made to create varieties by varying the thickness of the odor adsorbing membrane. In addition, elements having different resonance frequencies (for example, an overtone mode with varying thickness of the quartz crystal substrate) can also be used.

Regarding the type of the substrate, a silicon substrate, a substrate formed from a quartz crystal, a printed wiring substrate, a ceramic substrate, a resin substrate, and the like can be used. Furthermore, the substrate is a multilayer wiring substrate such as an interposer substrate, and an excitation electrode for self-exciting the quartz crystal substrate; a mounted wiring; and electrodes for electricity conduction are disposed on the substrate at arbitrary positions. The substrate is wired to, for example, bumps, for the purpose of electrical grounding or electrical conduction to other electronic circuit boards and the like.

Regarding the shape of the sensor element, for instance, a convex shape is a more preferable shape for the quartz crystal oscillator because the convex shape is smaller in size and prevents interference between various oscillators within the substrate by confining energy within each oscillator, and an increase in the Q value is anticipated.

A structure in which the quartz crystal oscillator is produced into a convex shape (lens shape or emboss shape) having a thickness distribution, one surface side thereof is provided with a separated type excitation electrode (electrode for inputting a voltage for oscillation), and an electroconductive membrane is installed at a position facing the opposite surface of the excitation electrode, can be adopted.

It is known that by adopting this structure, coupling with another oscillation mode can be suppressed, and interference such as propagation or reflection between quartz crystal oscillators occurring when the oscillators are arranged into a multi-array form can be prevented. Therefore, as further size reduction and further capacity reduction are achieved, the distance between the oscillators is shortened, and the effect is enhanced.

Similarly, the Q value and conductance can be increased by the oscillation energy confinement effect, and a quartz crystal oscillator which is not susceptible to an interference caused by external contact without a decrease in the oscillation energy even if the oscillator is miniaturized, can be obtained. As a result, the S/N ratio is increased, and the oscillator becomes highly sensitive.

When a QCM sensor formed herein has a structure called inverted mesa shape or a convex shape, since close surface mounting is enabled, the structure is suitable for miniaturization. In the present Examples, a convex type that is more suitable for a small-sized sensor is described as an example; however, if there is any other shape that is more optimal, that shape can be selected.

A convex hybrid shape obtained by inserting convexities into a concavity of the inverted mesa has also been attempted. Furthermore, increases in the sensitivity of QCM elements (Q values) can also be seen in an elliptical shape as well as a circular shape, and thus, a shape that is more optimal in the aspects of cost and the like may be used.

The size of the sensor main body (signal conversion unit) is preferably the same as, or even smaller than, the area where the substance adsorbing membrane has been applied on the surface of the sensor main body. Under the current technical restrictions, since there is a limitation in the reduction of the area of application of the substance adsorbing membrane, the sensor may be configured such that a plurality of sensor main bodies (signal conversion units) are assigned in the area where the substance adsorbing membrane has been applied. Regarding the structure of such a sensor main body (signal conversion unit), a transistor array composed of a plurality of fine MOSFET's, and a charge-coupled element array may be exemplified, and from the viewpoint of the ease of measurement and miniaturization, a charge-coupled element array is particularly preferred.

Thus far, configurations of sensor array in the odor sensor of the present invention has been illustrated, and it is needless to say that the present invention is not intended to be limited to these.

When such a configuration as described above is adopted, the odor sensor according to an embodiment can be operated on almost all odor substances as objects of detection, without limitations, as long as the odor substances are substances able to be adsorbed to the substance adsorbing membrane 103. Furthermore, based on such a configuration, a number of sensor elements required for detecting a number of substances that are desired to be detected and specified may be provided, and thereby, a plurality of odor substances included in an odor itself can be measured quantitatively and qualitatively. Thus, such odor can be comprehensively measured.

In the odor measurement system according to an embodiment, the sensor elements 101 that are disposed in the odor sensor 100 can be selected according to the substance to be measured. That is, sensor elements 101 based on a substance adsorbing membrane 103 having characteristics specific to an odor substance to be detected and measured; and a sensor main body 102 can be selected and disposed as appropriate.

Since the number of the sensor elements 101 is adjusted to at least two arrangements, the sensor elements can respectively specifically detect a plurality of odor substances included in an odor itself.

Furthermore, the detection sensitivity for each sensor element can also be varied by varying the characteristics, the membrane thickness or the like of the substance adsorbing membrane. Thereby, the concentration and the like of the odor substance as object of measurement can also be measured.

According to such a configuration, measurement is enabled for any odor substances existing in a gas as a sample. Furthermore, in conventional cases, only the intensity of an odor characteristic to the molecule could be measured from the amount of individual molecules simply included in an odor substance, or the like. However, odor substances measured from combinations of the detection patterns of sensors can be specified by measuring a specific odor, that is, the odor itself composed of a plurality of odor substances.

In regard to the odor sensor according to an embodiment, since the detection unit 1001 has odor sensors 100 in an array structure, the number of sensors that specifically act on particular substance molecules, the arrangement of the sensors, and the type of the sensors can be determined after arbitrarily designing the a reaction pattern for the array as a whole obtained through the operation of the sensors. Then, when the reaction pattern is stored in advance in an odor information storage unit 1004, the reaction pattern can be compared with the reaction at the odor sensor 100 for each of the odor substances. Therefore, a collection of a plurality of odor substances can be measured, and thereby, measurement of an odor itself including a plurality of odor substances, which could not be realized with conventional odor sensors, is now enabled.

<Method for Measuring Odor>

Next, an odor measuring method used according to an embodiment is explained.

First, an odor sensor 100 provided in the detection unit 1001 of the odor measurement system 1000 according to an embodiment as illustrated in FIG. 4 is brought into contact with an odor substance as an object of measurement. Through this contact, molecules of the odor substance are absorbed, and the substance is adsorbed to a substance adsorbing membrane 103 of the sensor element 101.

According to at least one embodiment, the odor sensor 100 has a multi-array structure in which at least two or more sensor elements 101 are disposed. Here, each sensor element 101 interact with each of intended odor substances to an extent characteristic to the odor substance, and the sensor element should interact with various odor causative substances included in an odor. The array part is brought into contact with a gas including adsorbed odor substances, and the results of the interaction exhibited by the respective sensors are obtained as data.

According to at least one embodiment, the interaction data may vary depending on the sensor used. The interaction data are physical information outputted from a transducer unit, such as emission responses, changes in the electrical resistance, or changes in the oscillation frequency.

A signal information retrieving process is performed at the measurement unit 1002 wherein the patterns of the interaction data are retrieved as signal information which is correlated with particularly measured odor factors and including the positional information of the responding sensors on the sensor array or the intensity of the interaction.

Subsequently, data processing of linking measurement data patterns with the arrangement information of the elements is performed at the data processing unit 1003.

That is, when this measurement data pattern obtained by performing data processing, for example, the output pattern illustrated in FIG. 4, is reproduced by means of the difference in the emission responses or is displayed as matrix information, thereby the odor itself can be visualized or made easily recognizable.

Furthermore, this data-processed interaction pattern information can be stored in a database together with information data related to odors by providing, for example, an odor information storage unit. The interaction pattern information can be utilized in the case of reproducing odors.

<Odor Sensor Arrangement Structure>

Figure 5:
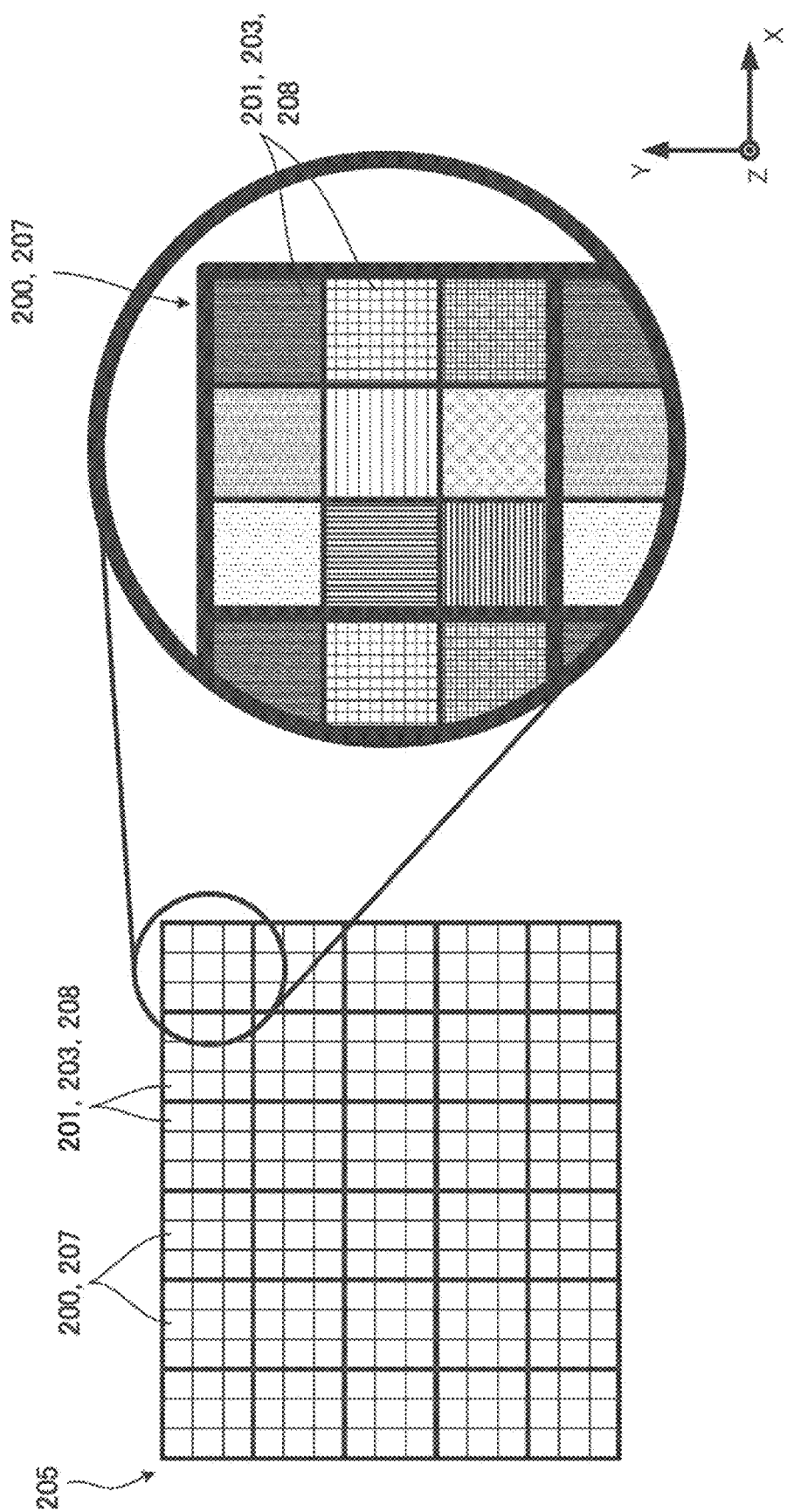
FIG. 5 is a schematic diagram of an odor sensor arrangement structure according to an embodiment and a partially magnified view of the same.

Next, an odor sensor arrangement structure 205 according to another embodiment is explained. FIG. 5 is a schematic diagram of the odor sensor arrangement structure 205 with a partially magnified diagram thereof. In FIG. 5, the partially magnified diagram including an odor sensor 200 disposed at the upper right corner of the odor sensor arrangement structure 205 and the vicinity thereof is illustrated inside the circle. FIG. 5 illustrates a case in which odor sensors 200 each have nine sensor elements planarly arranged in three columns in the Y-direction and three rows in the X-direction, and are planarly arranged in five columns in the Y-direction and six rows in the X-direction, so that thirty odor sensors in total are arranged. For each of the odor sensors 200, all of the nine sensor elements 201 have mutually different substance adsorbing membranes 203.

According to at least one embodiment, the odor sensor arrangement structure 205 includes two or more arranged units of the odor sensor 200 including sensor elements 201. An odor sensor 200 similar to the odor sensor 100 explained in a previously described embodiment can be used. The odor sensor includes two or more sensor elements 201, each of which has a substance adsorbing membrane 203 which adsorbs odor substances; and a signal conversion unit which determines the state of adsorption of the odor substances to the substance adsorbing membrane 203. The substance adsorbing membrane 203 contains an electroconductive polymer and a dopant which changes the substance characteristics of the electroconductive polymer. The respective substance adsorbing membranes 203 possessed by the two or more sensor elements have respectively different content ratios of the dopant with respect to the electroconductive polymer.

Since the odor sensor arrangement structure 205 has two or more arranged units of the odor sensor described above, the odor sensor arrangement structure 205 can detect the state of adsorption of an odor substance at two or more distinct positions. Thereby, the positional information of an odor substance or a gas including the odor substance can be detected.

Since the amount of adsorption of an odor substance to the substance adsorbing membrane 203 can be measured at two or more different positions, the direction of movement of the odor substance or a gas including the odor substance can be recognized based on the difference in the amount of adsorption of the odor substance at the respective odor sensors. That is, the direction of movement of the odor substance can be detected. For example, it may be considered that by detecting a so-called "burning smell" generated in a state of smoldering before ignition, or the like with an odor sensor arrangement structure 205, it can be detected from which direction the burning smell has moved, and thus the odor sensor arrangement structure 205 can be useful in specification of the site of ignition.

Furthermore, the measured values at the respective odor sensors of the odor sensor arrangement structure 205 can be recorded in a chronological order. Thereby, the path through which an odor substance has moved with a lapse of time can be recognized. Of course, the concentration distribution of the odor substance at positions corresponding to the respective odor sensors of the odor sensor arrangement structure 205 and the course of transition thereof can also be recognized.

The odor sensors 200 included in the odor sensor arrangement structure 205 may be identical or different; however, in the case of figuring out the direction of movement of a particular odor substance, it is preferable that the respective odor sensors 200 have in common at least one substance adsorbing membrane 203 that should be included in each of the odor sensors 200. Furthermore, it is more preferable that the respective odor sensors 200 have in common the combination of the substance adsorbing membranes 203 included in each of the odor sensors 200. Furthermore, it is preferable that the respective odor sensors 200 are identical.

According to at least one embodiment, the overall shape of the odor sensor arrangement structure 205 is not particularly limited; however, for example, as illustrated in FIG. 5, the odor sensor arrangement structure may be a planar-shaped odor sensor arrangement structure 205 in which various sensor elements 201 in each odor sensor are planarly arranged, and the respective odor sensors 200 are planarly arranged. When the overall shape of the odor sensor arrangement structure 205 is a planar shape, installation of the odor sensor arrangement structure at arbitrary planar-shaped places such as the wall, the ceiling, and the floor is facilitated.

According to at least one embodiment, the overall shape of the odor sensor arrangement structure 205 may also be a cylindrical shape or a spherical shape, both having the surface covered with odor sensors 200. By adopting an overall shape such as a cylindrical shape or a spherical shape as such, the direction of movement of an odor substance can be recognized three-dimensionally.

According to at least one embodiment, the method for producing the odor sensor arrangement structure 205 is not particularly limited; however, for example, in a case in which a transistor sensor array such as a charge-coupled element array or a MOSFET is used as the sensor main body (signal conversion unit), the transistor sensor array can be partitioned into compartments 207 in an area corresponding to odor sensors, each compartment 207 can be further partitioned into sub-compartments 208 in an area corresponding to sensor elements 201, and then respectively different substance adsorbing membranes 203 can be formed in each of the sub-compartments 208.

<Application Example of Odor Sensor Arrangement Structure>

An application example of the odor sensor arrangement structure 205 is explained with reference to FIG. 6 to FIG. 9. Here, an example of visualizing the measurement results obtained in various odor sensors 200 by using a flat-shaped odor sensor arrangement structure 205, in a case in which water and Japanese sake are respectively adsorbed or desorbed, is disclosed.

Figure 6:
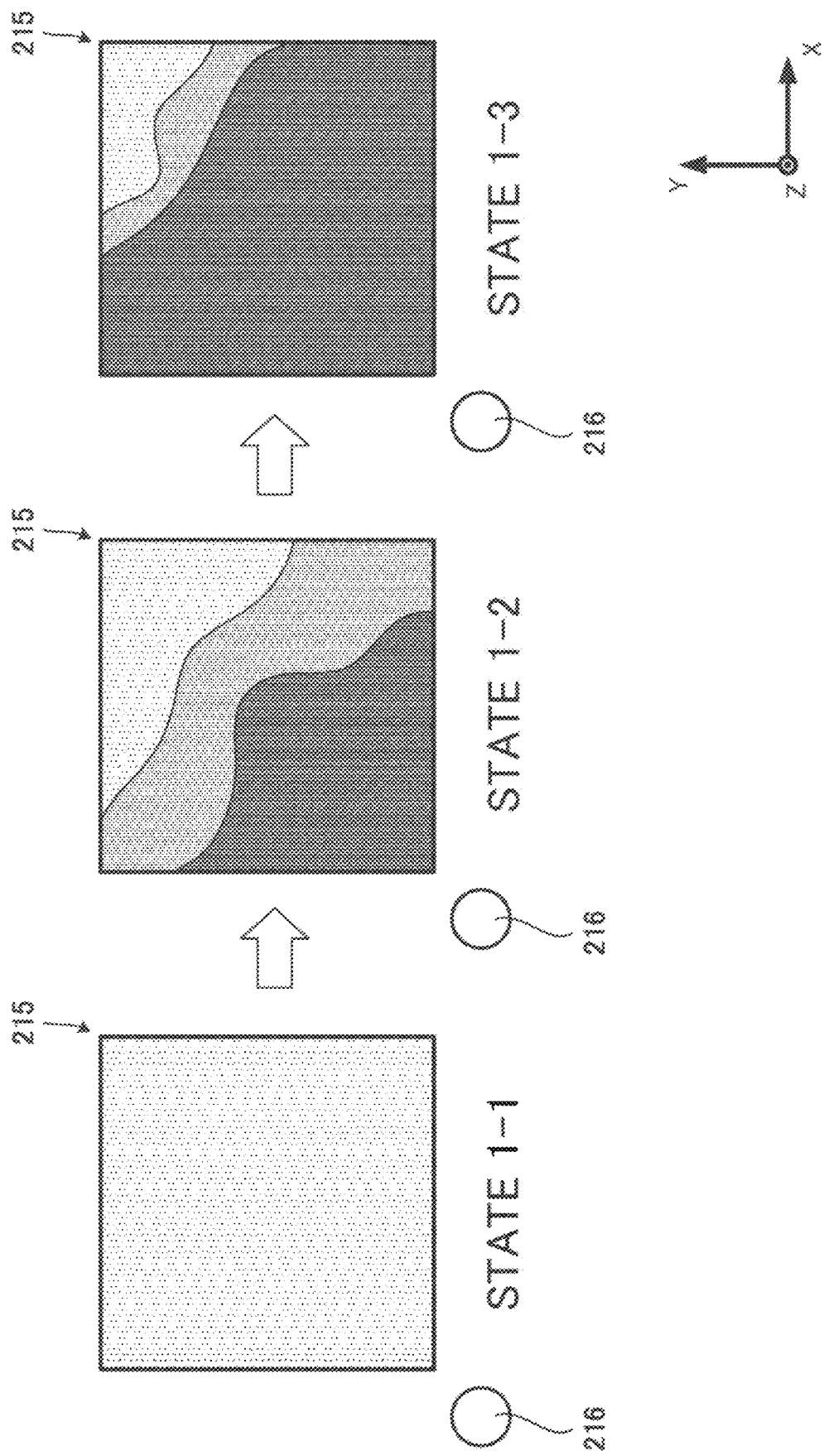
FIG. 6 is an explanatory diagram illustrating the changes in the state of adsorption occurring when water is adsorbed to a substance adsorbing membrane.
Figure 8:
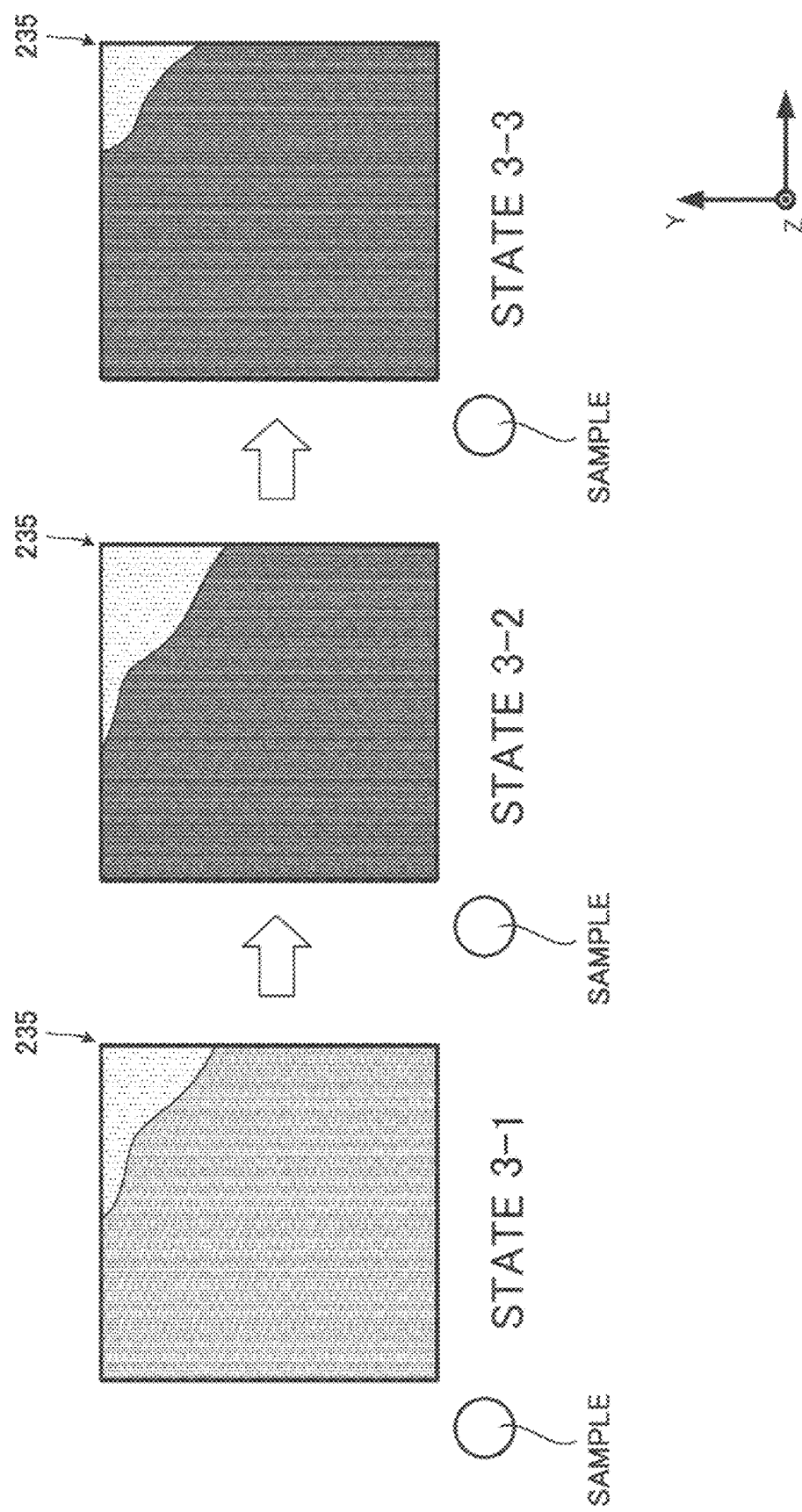
FIG. 8 is an explanatory diagram illustrating the changes in the state of adsorption occurring when Japanese sake is adsorbed to a substance adsorbing membrane.

FIG. 6 is an explanatory diagram illustrating changes in the state of adsorption occurring when water is adsorbed to the substance adsorbing membrane. FIG. 7 is an explanatory diagram illustrating changes in the state of desorption occurring when water is desorbed from the substance adsorbing membrane. FIG. 8 is an explanatory diagram illustrating changes in the state of adsorption occurring when Japanese sake is adsorbed to the substance adsorbing membrane. FIG. 9 is an explanatory diagram illustrating changes in the state of adsorption occurring when Japanese sake is desorbed from a substance adsorbing membrane. FIG. 6 to FIG. 9 illustrate the cases in which odor sensor arrangement structures 215, 225, 235, and 245 are provided on an X-Y plane, and water or Japanese sake contained in a sample container 216 or 236 is disposed at the position of a circle shown at the lower left of the odor sensor arrangement structure 215 or 235 in the diagram. The measurement results obtained immediately after disposing water or Japanese sake are indicated in FIG. 6 and FIG. 8 as "State 1-1" and "State 3-1", respectively. The measurement results obtained immediately after removing water or Japanese sake are indicated in FIG. 7 and FIG. 9 as "State 2-1" and "State 4-1", respectively. Measurement results obtained after a lapse of certain time after disposing or removing water or Japanese sake are indicated in FIG. 6 to FIG. 9 as "State 1-2", "State 2-2", "State 3-2", and "State 4-2", respectively. Furthermore, the measurement results obtained after a further lapse of certain time are indicated in FIG. 6 to FIG. 9 as "State 1-3", "State 2-3", "State 3-3", and "State 4-3", respectively.

Regarding a method for visualizing the measurement results obtained at the various odor sensors 200, the changes in the physical, chemical, or electrical characteristics of the various substance adsorbing membranes 203, which are attributed to the adsorption of an odor substance to the various substance adsorbing membranes 203, can be indicated by, for example, color discrimination or shade gradation depending on the magnitude of the amount of change. In FIG. 6 to FIG. 9, the measurement results are indicated by shade gradation depending on the magnitude of the amount of change. The shade gradation is shown to become darker as the amount of change increases, such that a case in which the amount of change is null (no change) or small is represented by a light shade; a case in which the amount of change is of a medium degree is represented by a shade of a medium degree; and a case in which the amount of change is large is represented by a dark shade. In FIG. 6 to FIG. 9, the shade is indicated in three levels for convenience; however, the threshold values for the change in color tone or the change in shade can be determined freely as appropriate.

In FIG. 6, at State 1-1 immediately after disposing water, the amount of change is null (no change) or small; however, at State 1-2 after a lapse of certain time, the region with a medium-level amount of change has progressed to about ⅔ from the lower left corner, and the region with a large amount of change has progressed to about ⅓ from the lower left corner. At State 1-3 after a further lapse of certain time, the amount of change has increased in most part of the odor sensor arrangement structure 215, and it is understood that the area in which the odor substance is adsorbed to the substance adsorbing membranes 203 of the various odor sensors 200 has been spread to most part of the odor sensor arrangement structure 215. Furthermore, the direction of movement of the odor substance can be determined by visualizing the changes in a chronological order as in the case of State 1-1 to State 1-3.

In FIG. 7, in State 2-1 immediately after removing water, there is almost no change from State 1-3 described above; however, it is understood that at State 2-2 and State 2-3 after a lapse of time, desorption of the odor substance proceeds along with evaporation of water, and the region with a large amount of change has been reduced.

In FIG. 8, at State 3-1 immediately after disposing Japanese sake, some volatile components included in Japanese sake have been adsorbed. It is understood that at State 3-2 and State 3-3 after a lapse of time, the region with a large amount of change has been expanded.

In FIG. 9, at State 4-1 immediately after removing Japanese sake, there is almost no change from State 3-3 described above. However, compared to the case of desorption of water, it is understood that the region in which the amount of the odor substance is still large is wide in State 4-2 and State 4-3.

As is obvious from a comparison between the changes in the state of adsorption at the time of adsorption and desorption of water in FIG. 5 and FIG. 6, and the changes in the state of adsorption at the time of adsorption and desorption of Japanese sake in FIG. 7 and FIG. 8, it is considered that the changes in the state of adsorption at the time of adsorption and desorption of an odor substance are specific to the odor substance. Therefore, discrimination of an odor substance or a collection of odor substances based on the odor pattern at the odor sensors 200 alone, as well as the changes over time in the state of adsorption detected using the odor sensor arrangement structures 215, 225, 235, and 245 can also be used for the discrimination of an odor substance or a collection of odor substances.

Since the various odor sensors 200 can detect odor patterns, the odor sensor arrangement structures 215, 225, 235, and 245 which include those odor sensors 200 can also detect the migration of two or more odor substances. Furthermore, in a case in which two or more odor substances are combined on the odor sensor arrangement structures 215, 225, 235, and 245, the odor sensors in the region where two or more odor substances have been combined can detect an odor pattern corresponding to the combined two or more odor substances. By applying these findings, for example, it is possible to perform qualitative and quantitative evaluations about what kind of odor would be obtained when fragrances are blended, and to visualize the evaluation results.

EXAMPLES

Hereinafter, the sensor elements having the substance adsorbing membranes of the odor sensor of the present invention are described in more detail by way of Examples.

Example 1 <Substance Adsorbing Membrane Based on Combination of Electroconductive Polymer and Ionic Liquid>

1) Preparation of Substance Adsorbing Membrane

In the present Example, preparation of a membrane solution such as described below was performed using polyaniline as an electroconductive polymer.

A solvent undiluted solution (2% polyaniline) was diluted 10 times with NMP (N-methyl-2-pyrrolidone). Subsequently, a dopant component was weighed such that the molar ratio of the dopant component would be 1.0 with respect to 2 units of aniline, and the dopant component described below was dissolved in NMP.

Next, the 0.2% polyaniline solution and the dopant solution were mixed at a ratio of 1:1.

System 1: 2% polyaniline only
System 5: Prepared by adding 1% 1-ethyl-3-methylimidazolium p-toluene sulfonate (anionic dopant) to 2% polyaniline, and mixing the mixture.
System 7: No membrane
Dopant: 1% 1-ethyl-3-methylimidazolium p-toluene sulfonate (anionic dopant)

2) Sample preparation: 0.1 μL of the membrane solution was applied onto the surface of a QCM sensor, and the applied membrane solution was dried in a drying furnace at 100° C. for 10 minutes to obtain a sensor element.

3) Experimental conditions: Temperature: 25° C., humidity: 55%

Gas: Air, $H_2O$, ethanol, $NH_3$

The concentrations of the sample gases were respectively 10 ppm.

Flow measurement: While the air inside the chamber was refreshed by introducing gases in the order of sample gas, air, sample gas, and air after every 300 seconds, subsequently stopping gas introduction, and then introducing air, changes in the frequency during the sample gas introduction were measured.

4) Results

Figure 10:
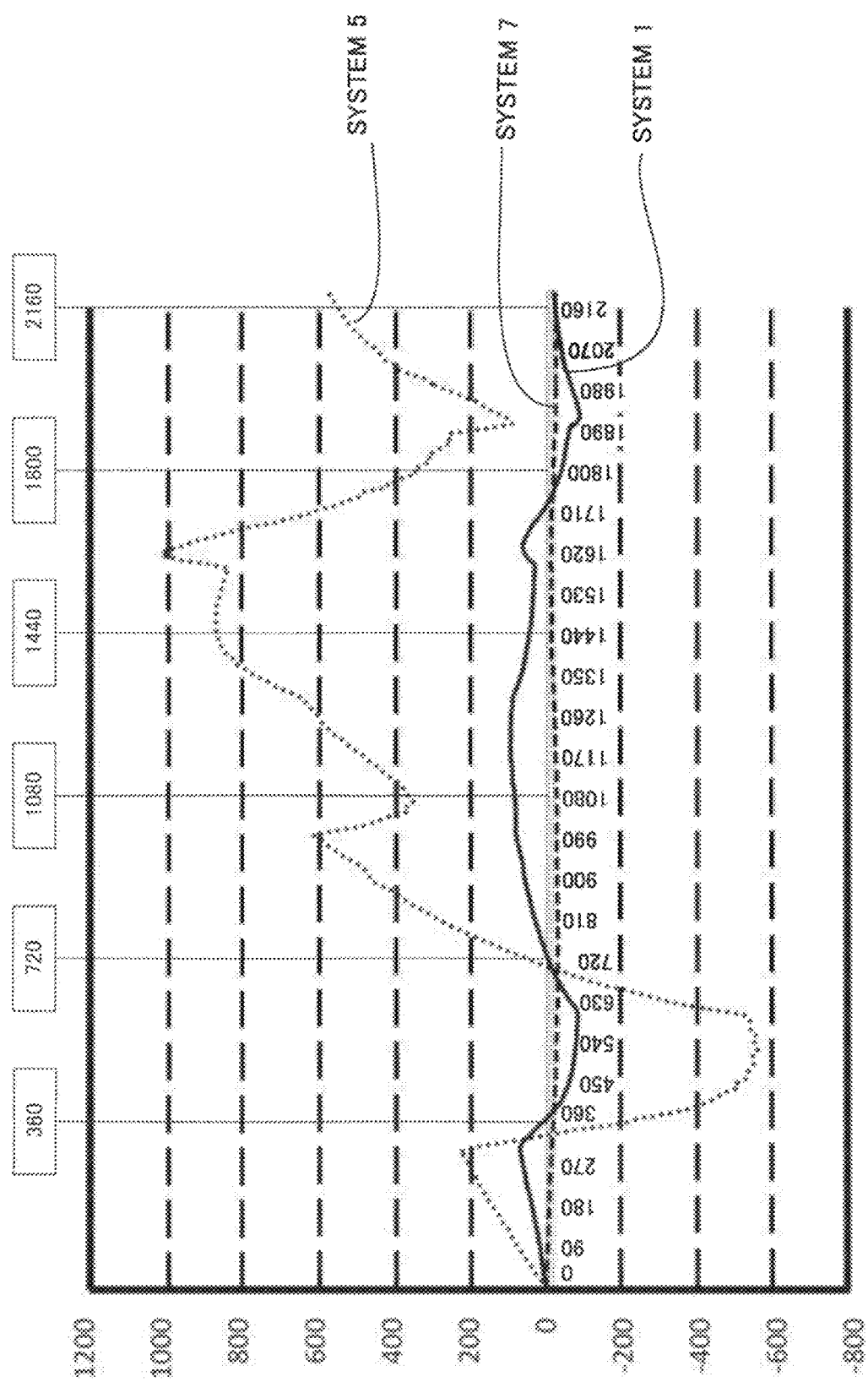
FIG. 10 is a graph showing the results of Example 1.

The results of the present experiment are presented in FIG. 10. The vertical axis represents changes in the frequency when the sensor responded, and the horizontal axis represents time. As shown in the graph, it was found that the sensor of System 5 provided with a dopant-containing substance adsorbing membrane responds specifically to each samples.

Example 2 (Comparative Example) <Test by Membrane Formation with Ionic Liquid Only>

A substance adsorbing membrane was produced from an ionic liquid, and tests were performed as follows.

1) Preparation of Membrane Solution

System 4: 0.00963 g of 1-butyl-3-methylimidazolium chloride was dissolved in 1 mL of ethanol, and then the solution was diluted to two times with ethanol.

System 7: 0.02138 g of 1-ethyl-3-methylimidazolium toluene sulfonate was dissolved in 1 mL of ethanol, and then the solution was diluted to two times with ethanol.

2) Sample Preparation

1 μL of each solutions of the respective systems described above was dropped on the surface of a QCM sensor using a micropipette. Next, drying was performed in a drying furnace at 100° C. for 10 minutes to obtain a membrane.

3) Conditions: Temperature 25° C., humidity 55%

Gas: $NH_3$ (10% $NH_3$, and water was introduced into a glass dish to adjust humidity), fragrance (obtained by dissolving 1 mL of musk in 40 mL of ethanol), air Flow measurement: The experiment was performed in the same manner as in Example 1.

4) Results

Figure 11:
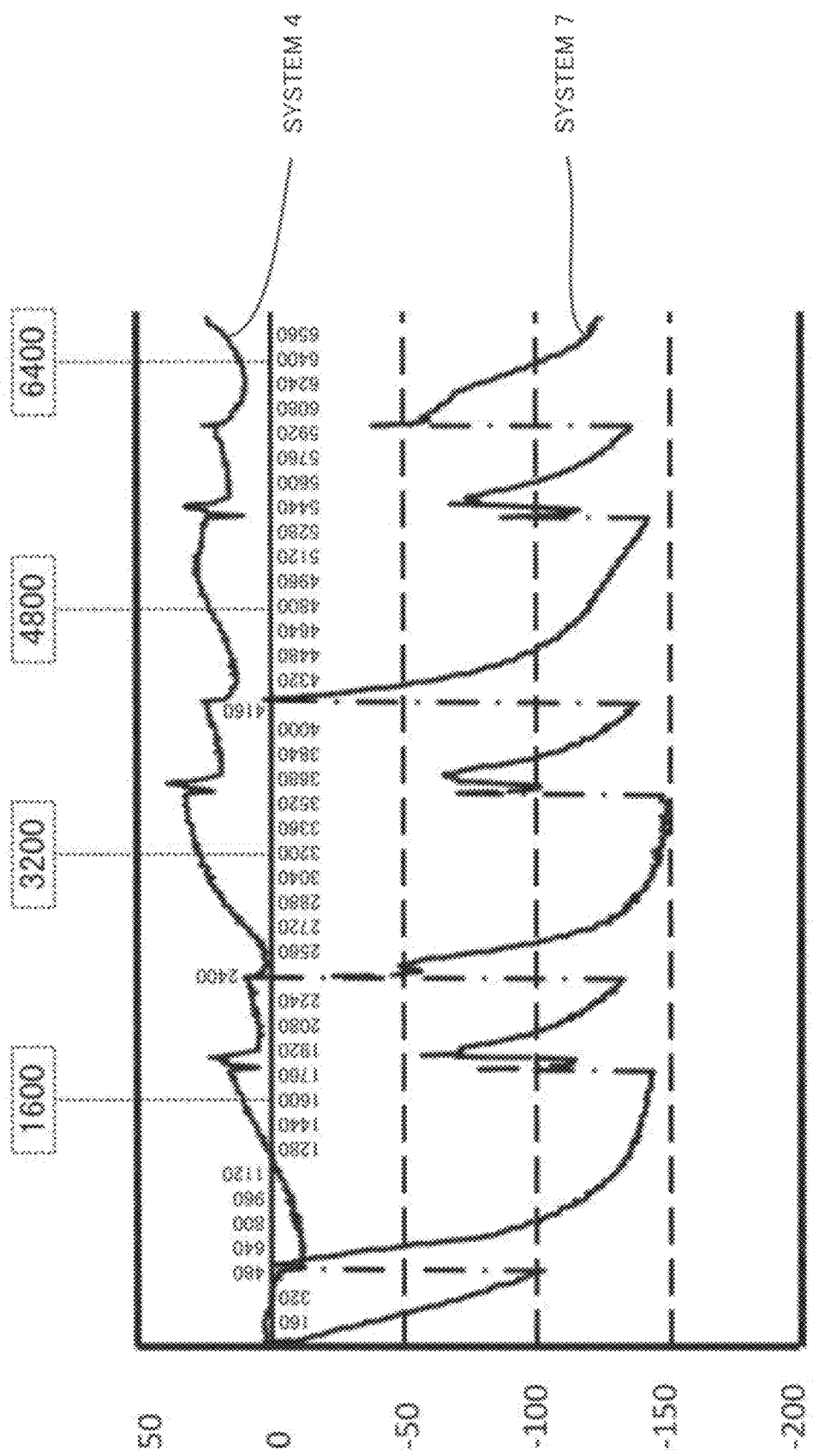
FIG. 11 is a graph showing the results of Example 2.
Figure 12:
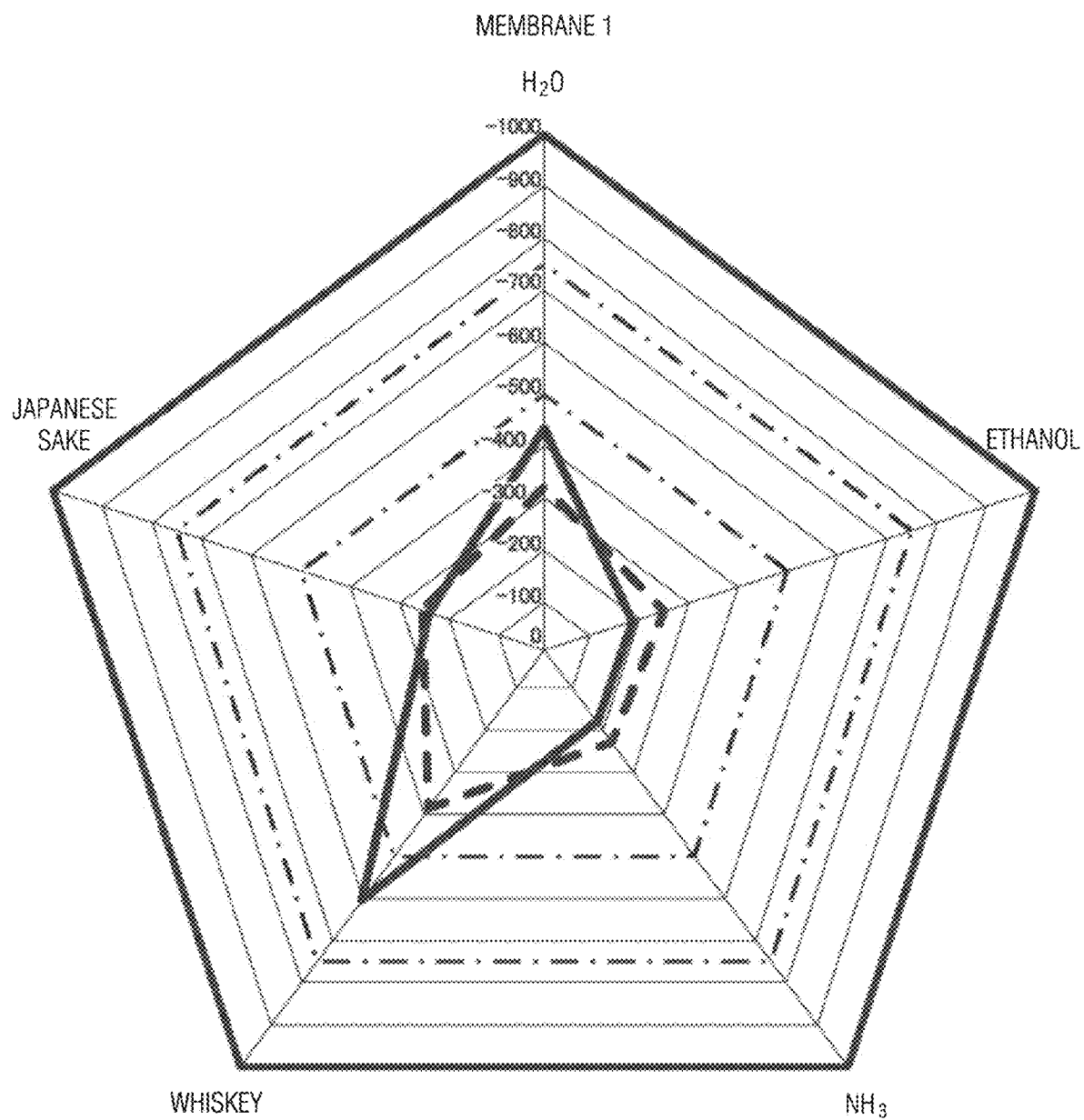
FIG. 12 is a radar chart showing Results 1 of Example 3.
Figure 13:
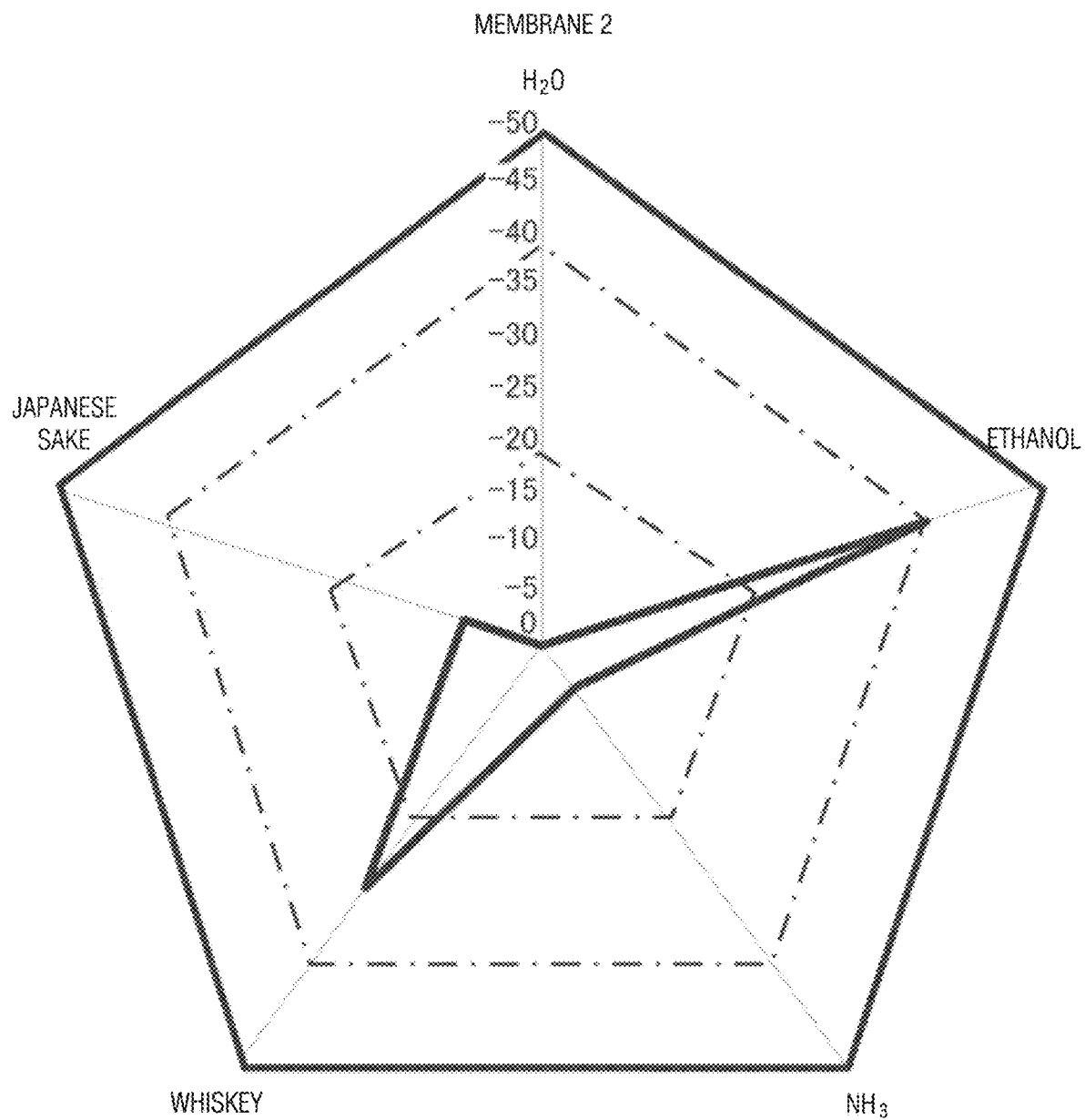
FIG. 13 is a radar chart showing Results 2 of Example 3.
Figure 14:
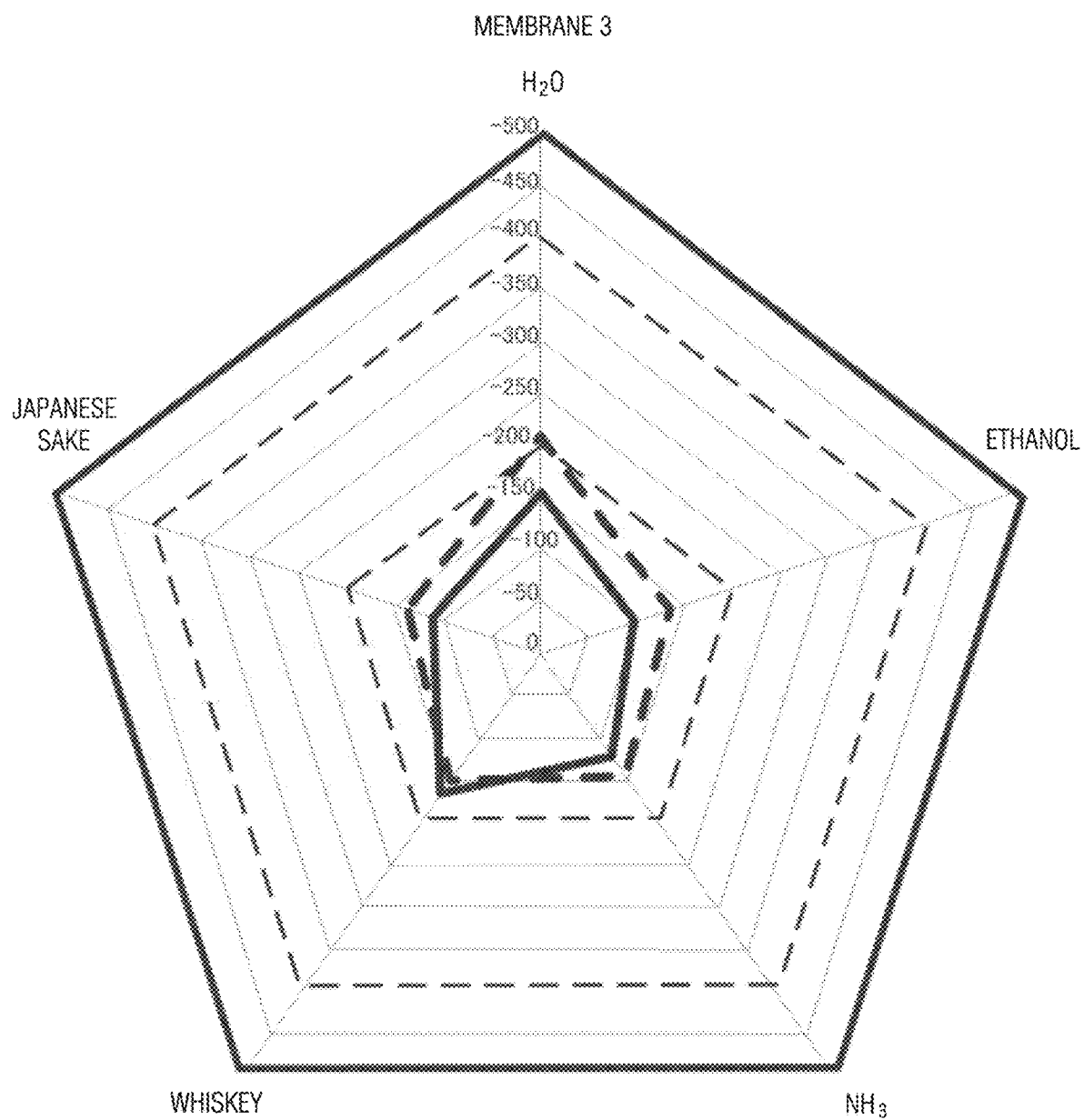
FIG. 14 is a radar chart showing Results 3 of Example 3.
Figure 15:
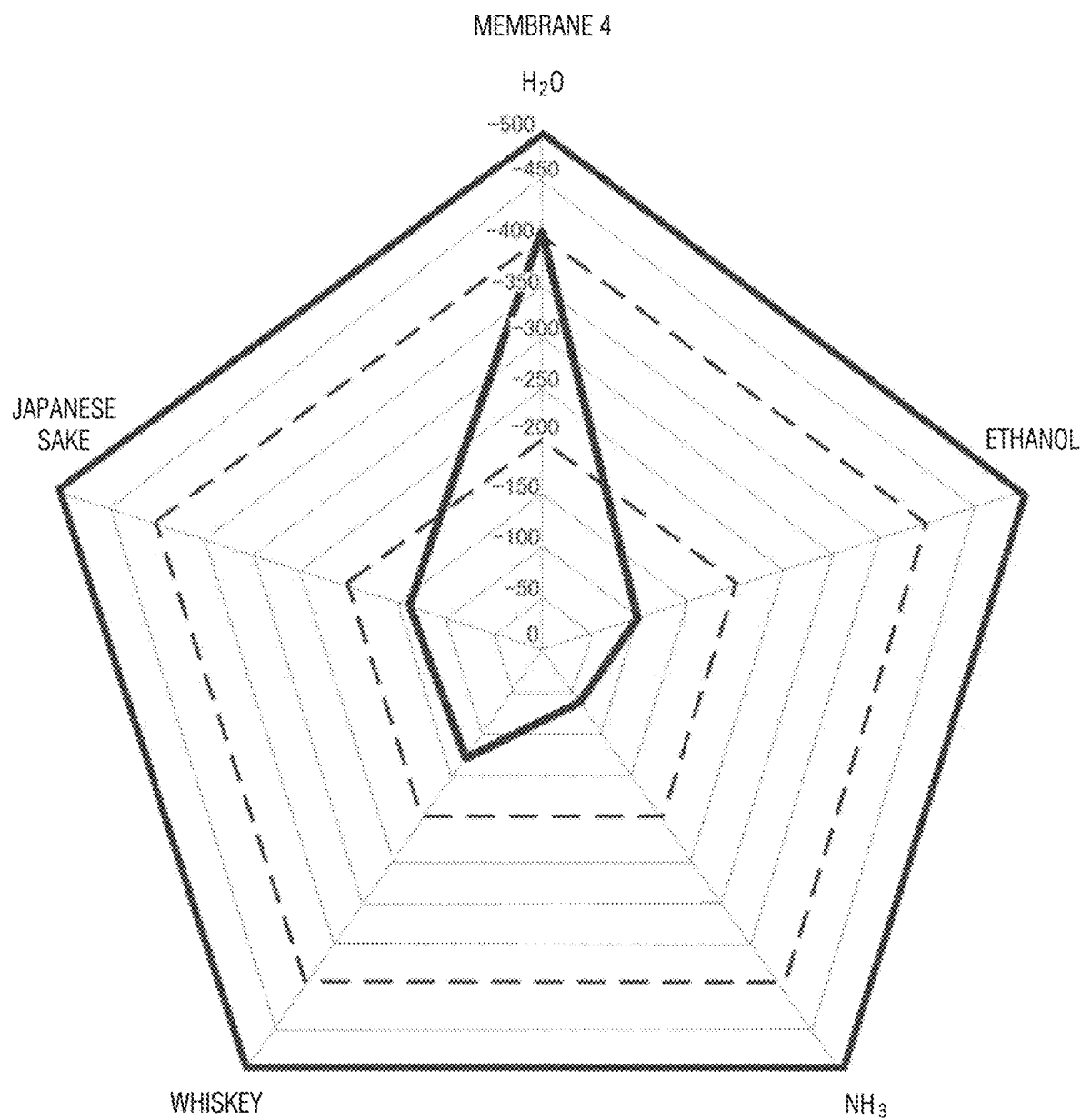
FIG. 15 is a radar chart showing Results 4 of Example 3.
Figure 16:
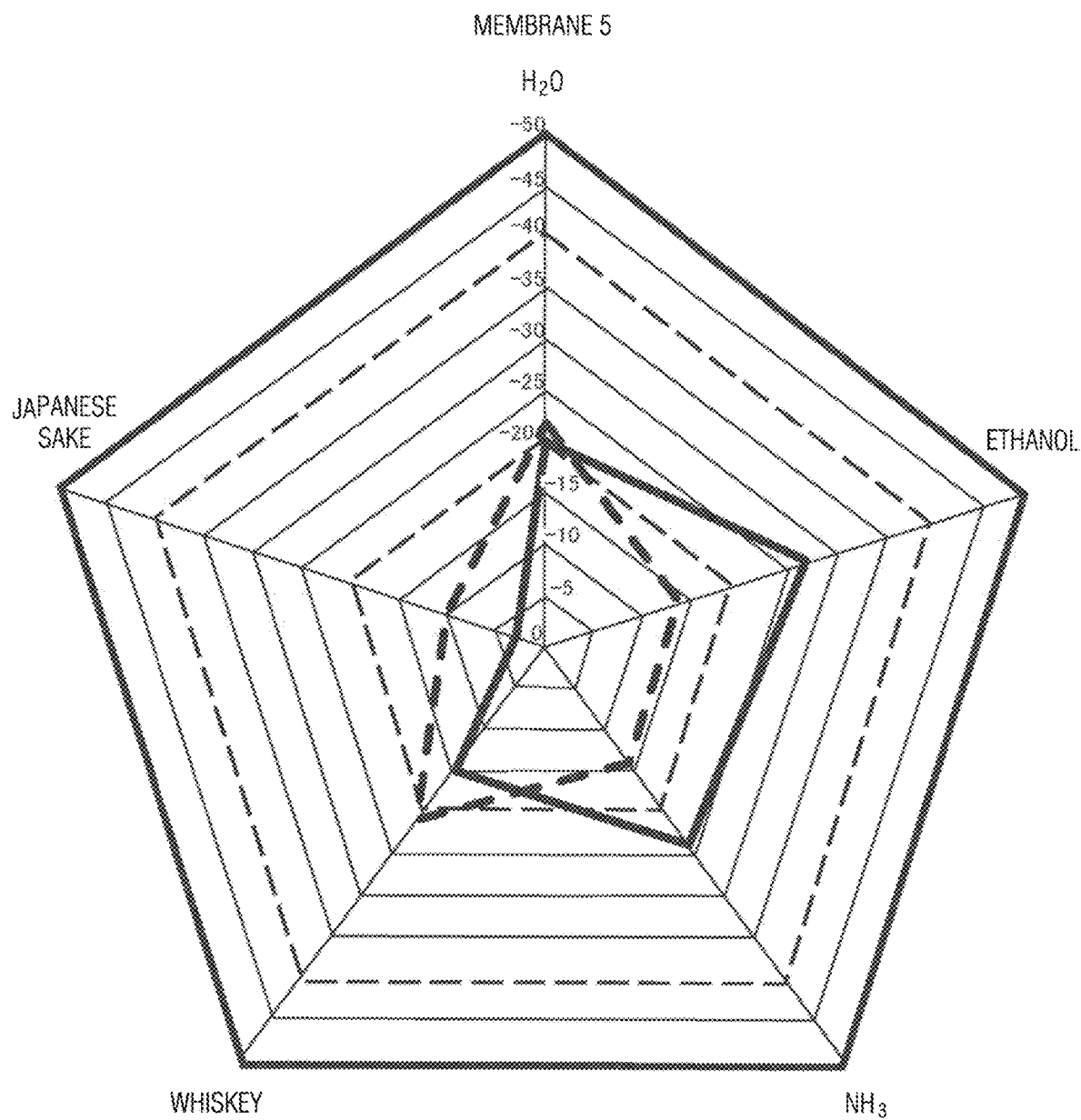
FIG. 16 is a radar chart showing Results 5 of Example 3.

The results of the present test are presented in FIG. 11. The vertical axis and the horizontal axis of the graph are similar to those of FIG. 10. As shown in the graph, responses occurred to some extent; however, it was not considered that the sensor exhibited a reaction specific to a particular substance.

Example 3

1) Preparation of Membrane Solution

Membrane solutions were prepared using 0.4% polyaniline, and mixing the polymer with the following ionic liquids as dopants.

A: 1-Butyl-3-methylimidazolium chloride (Wako Pure Chemical Industries, Ltd., 027-15201)

B: 1-Ethyl-3-methylimidazolium p-toluene sulfonate (Wako Pure Chemical Industries, Ltd., 051-07311)

C: Sodium dodecyl benzenesulfonate (soft type) (mixture) (62%, water-wetted product) (Tokyo Chemical Industry Co., Ltd. (TCI), D1238)

Membrane 1: 0.4% polyaniline+A
Membrane 2: 0.4% polyaniline+B
Membrane 3: 0.4% polyaniline+B+0.5% additives
Membrane 4: 0.4% polyaniline+B+2.0 additives
Membrane 5: 0.4% polyaniline+C+0.4% polyethylene dioxythiophene The preparation procedure was similar to that of Example 1.

2) Sample Preparation

Preparation was carried out in the same manner as in Example 1.

3) Experimental conditions: Temperature 25° C., humidity 55%

Sample gas: $H_2O$, ethanol, $NH_3$ (15 ppm), whiskey, Japanese sake

Flow measurement: The samples were volatilized, and the gases were caused to flow into the chamber while the air in the chamber was refreshed in the same manner as in Example 1 to perform the measurement.

4) Results

The results are presented in FIG. 12 to FIG. 16. FIG. 12 to FIG. 16 are radar charts showing the measurement results for various sample gases obtained with the Membranes 1 to 5 described above. As shown in the charts, it was found that when an ionic liquid as a dopant was mixed with polyaniline as an electroconductive polymer, the substance adsorption characteristics of the membranes changed according to the mixing conditions.

Thereby, it was found that odors can be measured in a manner specific to various substances, by changing the combination of the type, amount, and the like of the electroconductive polymer and the dopant.

Example 4

In Example 4, an evaluation was carried out for a case in which collections of odor substances of each of instant coffee and drip coffee were adsorbed to substance adsorbing membranes a to l produced using polyaniline as the electroconductive polymer and the following ionic liquids La to Ll as the dopant. Meanwhile, the preparation of the membrane solutions, sample production, and flow measurement were carried out substantially in the same manner as in Example 1, except that the ionic liquids were different.

1) Preparation of Membrane Solution

2% polyaniline as a raw material solution was diluted to ten times with NMP (N-methyl-2-pyrrolidone), and thereby a 0.2% polyaniline solution was prepared. Each of the ionic liquids listed below was weighed and dissolved in NMP, and ionic liquids La to Ll were prepared such that the molar ratio of the ionic liquid (dopant) component would be 1.0 with respect to 2 units of aniline. Next, the 0.2% polyaniline solution thus prepared was mixed with each of the ionic liquids La to Ll at a volume ratio of 1:1, and thus respective membrane solutions were prepared.

Ionic liquid La: 1-Butyl-3-methylimidazolium chloride

Ionic liquid Lb: 1-Ethyl-3-methylimidazolium p-toluene sulfonate

Ionic liquid Lc: Methane sulfonic acid

Ionic liquid Ld: Ammonium benzoate

Ionic liquid Le: Sodium laurate

Ionic liquid Lf: Ammonium (+)-3-bromocamphor-8-sulfonate

Ionic liquid Lg: Phosphoric acid

Ionic liquid Lh: 1-Ethyl-3-methylimidazolium sulfate

Ionic liquid Li: Acetic acid

Ionic liquid Lj: Boric acid

Ionic liquid Lk: Phenol

Ionic liquid Ll: Benzenesulfonic acid

2) Sample Preparation 0.1 μL of each of the membrane solutions thus prepared was applied by dropping on the surface of respective QCM sensors, and drying was performed in a drying furnace at a temperature of 100° C. for 10 minutes. Thus, sensor elements respectively having substance adsorbing membranes a to l were produced.

3) Experimental Conditions:

Temperature 25° C., humidity 55%

Sample gas: Powders of instant coffee and drip coffee were each placed in a sealed container for a certain time period, and the gases inside the sealed container were used as sample gases.

Flow measurement: Sample gases were sequentially introduced according to a cycle of introducing the sample gases into the chamber; the cycle including leaving the sample gas to stand for 300 seconds, and then introducing air for 300 seconds. Meanwhile, the chamber was refreshed by purging the sample gas inside the chamber by introducing air for 300 seconds.

4) Results

Figure 17:
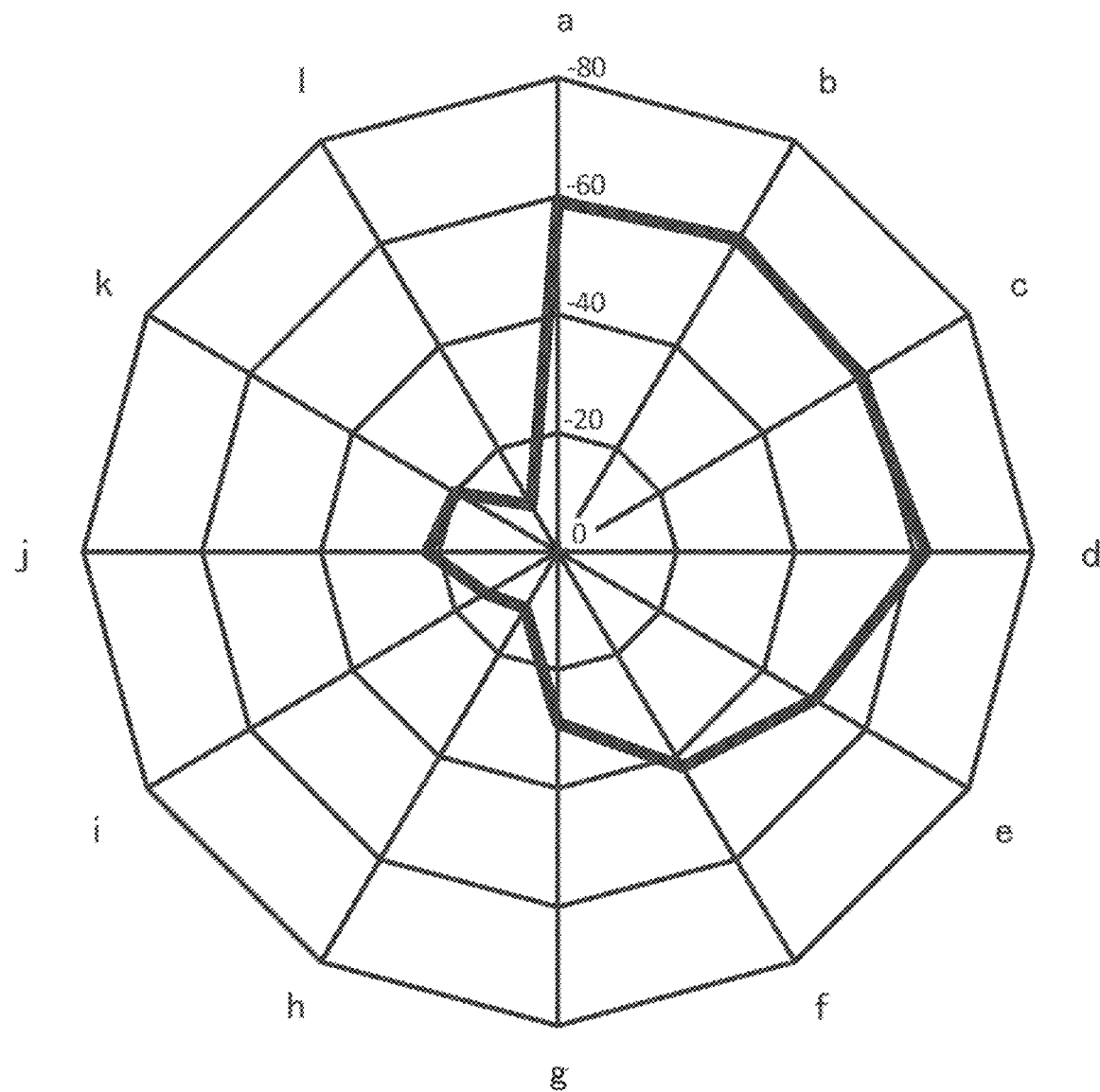
FIG. 17 is a radar chart showing Results 1 of Example 4.
Figure 18:
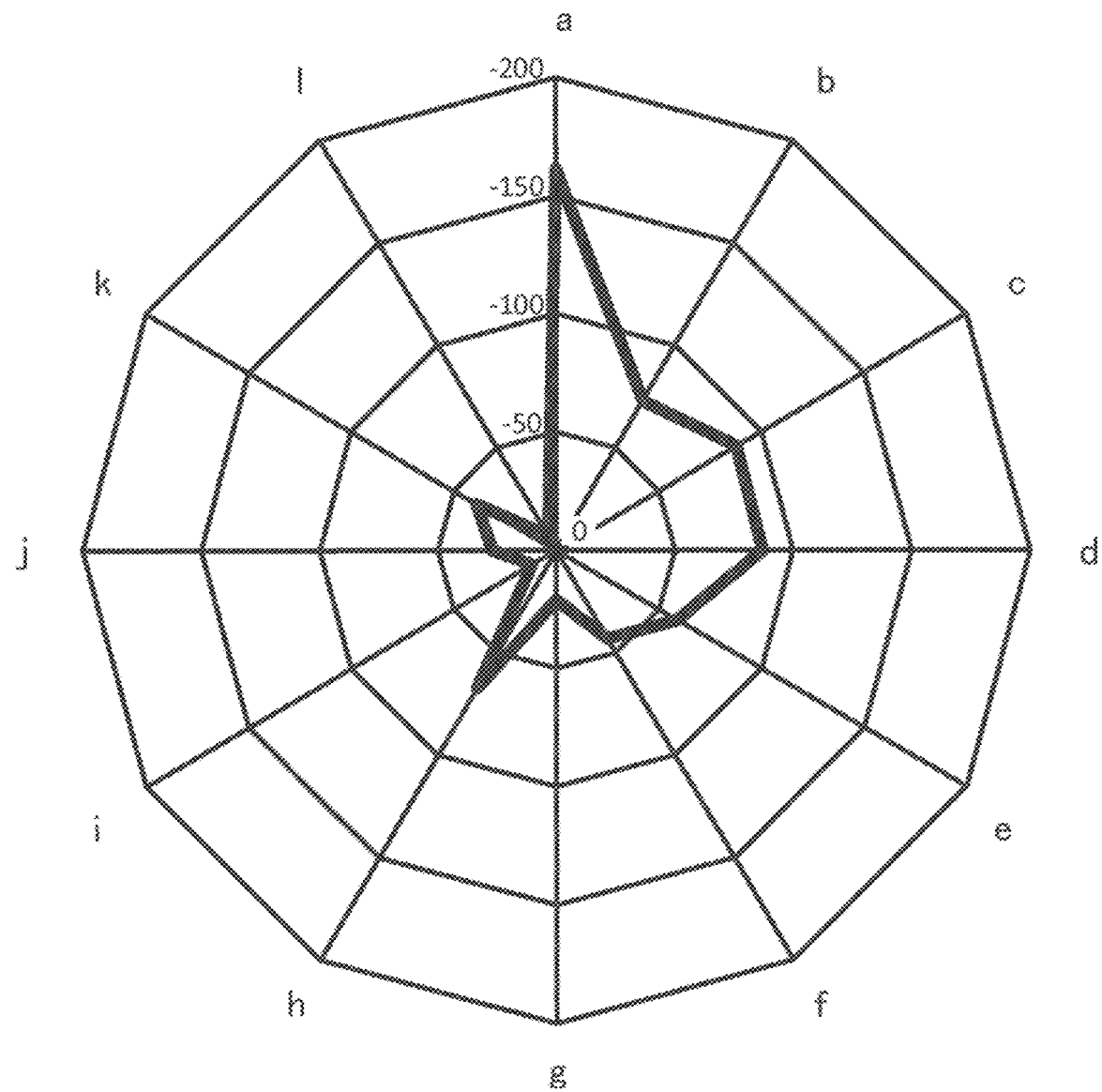
FIG. 18 is a radar chart showing Results 2 of Example 4.

Peak values of the changes in the frequency of the QCM sensors obtained by introducing a sample gas are presented in the radar chart of FIG. 17 or FIG. 18 as the measured values of Result 1 or Result 2, respectively. FIG. 17 is a radar chart showing Result 1 of Example 4, and shows the results obtained in a case in which a collection of odor substances from instant coffee was adsorbed to the substance adsorbing membranes a to l. FIG. 18 is a radar chart showing Result 2 of Example 4, and shows the results obtained in a case in which a collection of odor substances form drip coffee was adsorbed to the substance adsorbing membranes a to l.

Thus, sensor elements provided with substance adsorbing membranes have been explained using Examples; however, it is needless to say that the present invention is not intended to be limited to these Examples.

Unlike the conventional sensors that could detect only single substances of odor causative substances, a sensor based on sensor elements provided with the substance adsorbing membrane of the odor sensor of the present invention can detect the odor itself based on the detection pattern, even in a state in which a plurality of substances are mixed in a complicated manner, in other words, it is possible to provide a "second nose".

Therefore, the present invention is not intended to be used as a substitute for the gas sensors which are heavily used in chemical industries and the like, and the present invention can be used for patterning and analyses of odors in various fields such as, for example, quality management of products composed of a large number of various chemical species and have complicated odors, such as food products or beverages; replacement of sensory test for odorant products; and design of the odors of stationeries and daily goods. Thereby, sensing based on odors in a variety of circumstances is enabled.

For example, in the field of medicine, development of a technology of using the odor of the human body in the therapy and diagnosis of various diseases is currently underway, and the present invention can also be effectively utilized in such a field.

Alternatively, in the current IoT (Internet of Things) society, odors can be recorded based on the measurement of odor patterns using the odor sensor and the odor measurement system of the present invention, and an odor regeneration system in a virtual space can be provided based on the records of odors. Meanwhile, it is also possible to display odors as images in the case of online sales where users cannot perceive odors.

REFERENCE NUMERALS

100, 200: Odor sensor
101, 201: Sensor element
102: Sensor element main body
103, 203: Substance adsorbing membrane
205, 215, 225, 235, 245: Odor sensor arrangement structure
207: Compartment
208: Sub-compartment
216, 236: Sample container
1000: Odor measurement system
1001: Detection unit
1002: Measurement unit
1003: Data processing unit

What is claimed is:

1. An odor sensor, comprising:
three or more sensor elements, each sensor element having:
    a substance adsorbing membrane configured for adsorbing odor substances; and
    a signal conversion unit in the form of a surface acoustic wave sensor, a field effect transistor (FET) sensor, a charge coupled element sensor, a MOS field effect transistor sensor, a metal oxide semiconductor sensor, an organic electroconductive polymer sensor, or an electrochemical sensor configured for determining the state of adsorption of the odor substance to the substance adsorbing membrane,
    wherein the substance adsorbing membrane has an electroconductive polymer and a dopant configured for changing adsorption characteristics of the electroconductive polymer and the respective substance adsorbing membranes included in the three or more sensor elements have a thickness in the range of 10 nm to 10 μm and have respectively different content ratios of the dopant with respect to the electroconductive polymer, wherein the signal conversion unit detects a change in physical, chemical or electrical characteristics of the substance adsorbing membrane due to the adsorption of the substance thereto, and wherein the sensor elements are arranged planarly in the X-direction and the Y-direction.

2. The odor sensor according to claim 1, wherein the electroconductive polymer includes a π-electron conjugated polymer.

3. The odor sensor according to claim 2, wherein the π-electron conjugated polymer is selected from the group consisting of polypyrrole and derivatives thereof, polyaniline and derivatives thereof, polythiophene and derivatives thereof, polyacetylene and derivatives thereof, and polyazulene and derivatives thereof.

4. The odor sensor according to claim 1, wherein the dopant is an inorganic ion.

5. The odor sensor according to claim 4, wherein the inorganic ion is selected from the group consisting of chloride ion, oxychloride ion, bromide ion, sulfate ion, nitrate ion, and borate ion.

6. The odor sensor according to claim 1, wherein the dopant is an organic acid anion.

7. The odor sensor according to claim 6, wherein the organic acid anion is selected from the group consisting of an alkyl sulfonate, benzenesulfonate, and a carboxylate.

8. The odor sensor according to claim 1, wherein the dopant is a polymeric acid anion.

9. The odor sensor according to claim 8, wherein the polymeric acid anion is polyacrylate or polystyrene sulfonate.

10. The odor sensor according to claim 1, wherein the dopant is a salt.

11. The odor sensor according to claim 1, wherein the dopant is an ionic liquid.

12. The odor sensor according to claim 11, wherein the ionic liquid is a pyridine-based, alicyclic amine-based, or aliphatic amine-based ionic liquid.

13. An odor sensor arrangement structure, comprising:
two or more arranged odor sensors each including three or more sensor elements, each sensor element having a substance adsorbing membrane configured for adsorbing odor substances; and a signal conversion unit in the form of a surface acoustic wave sensor, a field effect transistor (FET) sensor, a charge coupled element sensor, a MOS field effect transistor sensor, a metal oxide semiconductor sensor, an organic electroconductive polymer sensor, or an electrochemical sensor configured for determining the state of adsorption of the odor substance to the substance adsorbing membrane,
wherein the substance adsorbing membrane has an electroconductive polymer and a dopant configured for changing adsorption characteristics of the electroconductive polymer, and the respective substance adsorbing membranes included in the three or more sensor elements have a thickness in the range of 10 nm to 10 μm and have respectively different content ratios of the dopant with respect to the electroconductive polymer, wherein the signal conversion unit detects a change in physical, chemical or electrical characteristics of the substance adsorbing membrane due to the adsorption of the substance thereto, and wherein the sensor elements are arranged planarly in the X-direction and the Y-direction.

14. The odor sensor arrangement structure according to claim 13, wherein the direction in which the odor substance has approached to the odor sensors, based on the differences in the amount of adsorption of the odor substance at the respective odor sensors is detected by the two or more arranged odor sensors.

15. The odor sensor arrangement structure according to claim 13, wherein the two or more odor sensors respectively have the same combination of the substance adsorbing membranes.

16. The odor sensor arrangement structure according to claim 13, wherein the arrangement of the respective sensor elements is the same in each of the two or more odor sensors.

17. The odor sensor arrangement structure according to claim 13, wherein the two or more odor sensors are planarly arranged.

18. An odor measurement system, comprising:
a detection unit having an odor sensor including three or more sensor elements configured for interaction with an odor substance;
a data processing unit configured for patterning the electrical characteristics of the respective sensor elements based on the interaction between the sensor elements and the odor substance, and visualizing the pattern; and
an analysis unit configured for analyzing and recognizing the pattern,
wherein the odor sensor includes the three or more of the sensor elements each having a substance adsorbing membrane configured for adsorbing the odor substances; and a signal conversion unit in the form of a surface acoustic wave sensor, a field effect transistor (FET) sensor, a charge coupled element sensor, a MOS field effect transistor sensor, a metal oxide semiconductor sensor, an organic electroconductive polymer sensor, or an electrochemical sensor configured for determining the state of adsorption of the odor substance to the substance adsorbing membrane,
wherein the substance adsorbing membrane has an electroconductive polymer and a dopant configured for changing adsorption characteristics of the electroconductive polymer,
wherein the respective substance adsorbing membranes included in the three or more sensor elements have a thickness in the range of 10 nm to 10 μm and have respectively different content ratios of the dopant with respect to the electroconductive polymer, and
wherein the signal conversion unit detects a change in physical, chemical or electrical characteristics of the substance adsorbing membrane due to the adsorption of the substance thereto, and
wherein the sensor elements are arranged planarly in the X-direction and the Y-direction.

* * * * *